(12) United States Patent
Baranyi

(10) Patent No.: US 11,918,624 B2
(45) Date of Patent: Mar. 5, 2024

(54) THERAPEUTIC COMPOSITION FOR USE IN THE TREATMENT OF COVID-19 AND OTHER CYTOKINE STORM ASSOCIATED DISORDERS

(71) Applicant: Kelsius Laboratories LLC, Baltimore, MD (US)

(72) Inventor: Lajos Baranyi, Gaithersburg, MD (US)

(73) Assignee: Kelsius Laboratories LLC, Baltimore, MD (US)

( * ) Notice: Subject to any disclaimer, the term of this patent is extended or adjusted under 35 U.S.C. 154(b) by 0 days.

(21) Appl. No.: 16/898,378

(22) Filed: Jun. 10, 2020

(65) Prior Publication Data

US 2021/0386821 A1    Dec. 16, 2021

(51) Int. Cl.
*A61K 38/17*        (2006.01)
*A61K 38/18*        (2006.01)
(Continued)

(52) U.S. Cl.
CPC ...... *A61K 38/1709* (2013.01); *A61K 38/1875* (2013.01); *A61K 38/4813* (2013.01);
(Continued)

(58) Field of Classification Search
CPC .. A61K 2300/00; A61K 9/0019; A61K 38/00; A61K 38/1709; A61K 38/1875;
(Continued)

(56) References Cited

U.S. PATENT DOCUMENTS 4,079,125 A  *  3/1978  Sipos ................... A61K 9/2022
                                                424/480
4,171,299 A     10/1979  Hamburger
(Continued)

FOREIGN PATENT DOCUMENTS

AU         628910 B2    9/1992
AU       2003215446 B2    3/2009
(Continued)

OTHER PUBLICATIONS

GenBank AAA85332.1, Complement component C3 [*Homo sapiens*], GenBank AAA85332.1, NCBI.NLM.NIH.GOV, 2 pages (Jan. 10, 1996), also available at https://www.ncbi.nlm.nih.gov/protein/AAA85332.1 (Year: 1996).*

(Continued)

*Primary Examiner* — Randall L Beane
(74) *Attorney, Agent, or Firm* — Faegre Drinker Biddle & Reath LLP

(57) ABSTRACT

It is disclosed a therapeutic composition for use in the treatment of COVID-19 and other cytokine storm associated disorders, wherein the therapeutic composition comprises at least one active agent being selected from the following active agent groups a) to e):

a) complement factor 3-targeting inhibitor of complement activation cascade b) carboxypeptidase B enzyme c) complement factor 5a receptor-targeting inhibitor of complement activation cascade d) endothelin A receptor-targeting inhibitor of extravasation e) bone morphogenic protein.

It is further disclosed a method of treating COVID-19 and other cytokine storm associated disorders, wherein said method comprises administering an effective amount of at least one active agent being selected from the above mentioned active agent groups a) to e).

7 Claims, 5 Drawing Sheets

Specification includes a Sequence Listing.

(51) Int. Cl.
    *A61K 38/48* (2006.01)
    *C12N 15/86* (2006.01)
    *A61K 45/06* (2006.01)
(52) U.S. Cl.
    CPC .............. *C12N 15/86* (2013.01); *A61K 45/06* (2013.01); *C12Y 304/17002* (2013.01)
(58) Field of Classification Search
    CPC ................ A61K 38/4813; A61K 45/06; C07K 14/4703; C12N 15/86; C12Y 304/17002
    See application file for complete search history.

(56) References Cited

U.S. PATENT DOCUMENTS

| | | | |
|---|---|---|---|
| 4,692,511 A | 9/1987 | Hahn | |
| 5,011,825 A | 4/1991 | Konig et al. | |
| 5,171,739 A | 12/1992 | Scott et al. | |
| 5,547,939 A | 8/1996 | Selsted | |
| 5,614,370 A | 3/1997 | Konteatis et al. | |
| 5,807,824 A | 9/1998 | van Oostrum et al. | |
| 5,837,499 A | 11/1998 | van Oostrum et al. | |
| 5,837,686 A | 11/1998 | Kirby et al. | |
| 5,849,297 A * | 12/1998 | Harrison ................. | A61P 37/00 424/178.1 |
| 5,948,668 A * | 9/1999 | Hartman ................ | C07K 14/62 435/212 |
| 7,553,931 B2 * | 6/2009 | Kolln ...................... | A61P 19/02 530/350 |
| 7,763,708 B2 | 7/2010 | Okada et al. | |
| 7,786,084 B2 | 8/2010 | Benner et al. | |
| 9,289,467 B2 | 3/2016 | Lin et al. | |
| 9,907,838 B2 | 3/2018 | Kim | |
| 10,238,735 B2 * | 3/2019 | Bredehorst .......... | A61K 9/0024 |
| 2005/0154191 A1 * | 7/2005 | Steward ............... | C07K 14/472 530/350 |
| 2006/0234921 A1 | 10/2006 | Shiels et al. | |
| 2006/0275826 A1 | 12/2006 | Okada et al. | |
| 2008/0161232 A1 | 7/2008 | Hummel et al. | |
| 2008/0220003 A1 | 9/2008 | Schnatbaum et al. | |
| 2014/0371133 A1 | 12/2014 | Francois et al. | |
| 2016/0082089 A1 | 3/2016 | Kim | |
| 2019/0328865 A1 * | 10/2019 | Du ........................... | C12N 7/00 |

FOREIGN PATENT DOCUMENTS

| | | | |
|---|---|---|---|
| CN | 103796667 A | 5/2014 | |
| EP | 1739078 A1 | 1/2007 | |
| EP | 1 739 078 A1 | 9/2020 | |
| GR | 900100052 A | 6/1991 | |
| JP | 2003-313200 A | 11/2003 | |
| JP | 2008526915 A | 7/2008 | |
| TW | 1653980 B | 3/2019 | |
| WO | WO-90/09162 A2 | 8/1990 | |
| WO | WO-92/012168 A1 | 7/1992 | |
| WO | WO-92/021361 A1 | 12/1992 | |
| WO | WO-93/011153 A1 | 6/1993 | |
| WO | WO-93/011784 A1 | 6/1993 | |
| WO | WO-9701578 A1 * | 1/1997 | ........... C07K 14/472 |
| WO | WO-03/086448 A1 | 10/2003 | |

OTHER PUBLICATIONS

Bialy et at., Formulation, Delivery and Stability of Bone Morphogenetic Proteins for Effective Bone Regeneration, Pharm Res, vol. 34:1152-1170 (Mar. 24, 2017) (Year: 2017).*

Nilsson et al., Neoantigens in complement component C3 as detected by monoclonal antibodies, Biochem. J., vol. 268:55-61 (1990); (Year: 1990).*

Baranyi et al., The antisense homology box: A new motif within proteins that encodes biologically active peptides, Nature Medicine, vol. 1(9):894-901 (Sep. 1995) (Year: 1995).*

Zhang et al., Absence of complement component 3 does not prevent classical pathway-mediated hemolysis, Blood Advances, vol. 3 (12):1808-1814 (Jun. 25, 2019) (Year: 2019).*

Dhingra et al., Kimura disease: case report and brief review of the literature; Medicine and Pharmacy Reports, vol. 92(2):195-199 (Apr. 25, 2019) (Year: 2019).*

Harris et al., Expanding horizons in complement drug discovery: challenges and emerging strategies, Semin. Immunopathol., vol. 40:125-140 (Oct. 6, 2017) (Year: 2017).*

Carpanini et al., Therapeutic Inhibition of the Complement System in Diseases of the Central Nervous System, Frontiers in Immunology, vol. 10(article 362):1-17 (Mar. 4, 2019) (Year: 2019).*

Asai et al., "Procarboxypeptidase R Deficiency Causes Increased Lethality in Concanavalin A-Induced Hepatitis in Female Mice," *Biol. Pharm. Bull.* 2010, vol. 33, No. 7, pp. 1256-1259.

Baranyi et al., "Antisense homology boxes in C5a receptor and C5a anaphylatoxin: a new method for identification of potentially active peptides," The Journal of Immunology, 1996, vol. 157, pp. 4591-4601.

Baranyi et al., "The antisense homology box: A new motif within proteins that encodes biologically active peptides," Nature Medicine, Sep. 1995, vol. 1, No. 9, pp. 894-901.

Baranyi et al., "Antisense homology boxes coincide with the "hot spot" regions predicted by resonant recognition theory," 2nd International Conference on Bioelectromagnetism , Feb. 1998, Melbourne Australia, pp. 67-68.

Baranyi et al., "Membrane-bound complement regulatory activity is decreased on vaccinia virus-infected cells," Clin. Exp. Immunol. 1994, vol. 98, pp. 134-139.

Cook et al., "Structure of human desArg-C5a," Acta Cryst. 2010, D66, pp. 190-197.

Farkas et al., "Complement C5a Receptor-Mediated Signaling May Be Involved in Neurodegeneration in Alzheimer's Disease," The Journal of Immunology 2003, vol. 170, pp. 5764-5771; doi:10.4049/jimmunol.170.11.5764; http://www.jimmunol.org/content/170/11/5764.

Farkas et al., "A complement C5a fragment peptide causes apoptosis in TGW neuroblastoma cells," 1996, Fifth International Conference On Alzheimer's Disease, S183.

Szebeni et al., "Hypersensitivity To Taxol and Doxil: Experimental and Clinical Evidence for a Causal Role of Complement Activation," Circulation 1999, vol. 99, p. 2302.

Kazatchkine et al., "Activation of the complement system at the interface between blood and artificial surfaces," Biomaterials, Jan. 1998, vol. 9, pp. 30-35.

Maglakelidze et al., "A Review: Does Complement or the Contact System Have a Role in Protection or Pathogenesis of COVID-19?" Pulm Ther May 13, 2020; https://doi.org/10.1007/s41030-020-00118-5.

Rathbone et al., "A systematic review of eculizumab for atypical haemolytic uraemic syndrome (aHUS)," 2013, *BMJ Open* 2013;3:e003573. doi:10.1136/bmjopen-2013-003573.

Sato et al., "Pro-Carboxypeptidase R is an Acute Phase Protein in the Mouse, Whereas Carboxypeptidase N Is Not," *J Immunol* 2000, vol. 165, pp. 1053-1058. doi. 10.4049/jimmunol.165.2.1053; http://www.jimmunol.org/content/165/2/1053.

Szebeni et al., Role of Complement Activation in Hypersensitivity Reactions To Doxil and Hynic PEG Liposomes: Experimental and Clinical Studies, Journal of Liposome Research 2002, vol. 12 (1&2), pp. 165-172.

Szebeni et al., "Hemodynamic Changes Induced by Liposomes and Liposome-Encapsulated Hemoglobin in Pigs; A Model for Pseudoallergic Cardiopulmonary Reactions to Liposomes: Role of Complement and Inhibition by Soluble CR1 and Anti-C5a Antibody," *Circulation* 1999, vol. 99, pp. 2302-2309.

Szebeni et al., "Liposome-induced pulmonary hypertension: properties and mechanism of a complement-mediated pseudoallergic reaction," American Journal of Physiology-Heart and Circulatory Physiology 2000, vol. 279, Issue 3; pp. H1319-H1328.

Campbell et al., "Carboxypeptidase R is an inactivator of complement-derived inflammatory peptides and an inhibitor of fibrinolysis," Immunological Reviews 2001, vol. 180, pp. 162-167.

(56) References Cited

OTHER PUBLICATIONS

Zeisberg et al., "Are there endogenous molecules that protect kidneys from injury? The case for bone morphogenic protein-7 (BMP-7)," Nephrol Dial Transplant 2004, vol. 19, pp. 759-761; doi: 10.1093/ndt/gfh060.
Dituri et al. The Interactivity between TGFβ and BMP Signaling in Organogenesis, Fibrosis, and Cancer. Cells. 2019;8(10):1130. Published Sep. 23, 2019. doi:10.3390/cells8101130, Sep. 10, 2020 [reference "H" in IDS filed Sep. 10, 2020].
Fletcher-Sandersjöö et al. Does Complement-Mediated Hemostatic Disturbance Occur in Traumatic Brain Injury? A Literature Review and Observational Study Protocol. Int J Mol Sci. 2020;21(5):1596. Published Feb. 26, 2020. doi:10.3390/ijms21051596, Sep. 10, 2020 [reference "J" in IDS filed Sep. 10, 2020].
Kay et al. Distribution, dynamics and functional roles of phosphatidylserine within the cell. Cell Commun Signal 17, 126 (2019). Published Oct. 15, 2019 https://doi.org/10.1186/s12964-019-0438-z, Sep. 10, 2020 [reference "M" in IDS filed Sep. 10, 2020].
Nagata et al. Flippase and scramblase for phosphatidylserine exposure. Curr Opin Immunol. Feb. 2020;62:31-38. doi: 10.1016/j.coi.2019.11.009. Epub Dec. 11, 2019. PMID: 31837595, Sep. 10, 2020 [reference "P" in IDS filed Sep. 10, 2020].
Szebeni et a. Human Clinical Relevance of the Porcine Model of Pseudoallergic Infusion Reactions. Biomedicines. 2020;8(4):82. Published Apr. 8, 2020. doi:10.3390/biomedicines8040082, Sep. 10, 2020 [reference "V" in IDS filed Sep. 10, 2020].
Vreede et al. Cryptic conspirators: a conversation about thrombocytopenia and antiphospholipid syndrome. Curr Opin Rheumatol. May 2019;31(3):231-240. doi: 10.1097/BOR.0000000000000595. PMID: 30747734; PMCID: PMC6455093, Sep. 10, 2020 [reference "W" in IDS filed Sep. 10, 2020].
Waisayarat et a1. Intracardiac thrombus in a patient with catastrophic antiphospholipid syndrome: an autopsy case report and review of the literature. Vasc Health Risk Manag. 2019;15:253-258. Published Aug. 7, 2019. doi:10.2147/VHRM.S197638, Sep. 10, 2020 [reference "X" in IDS filed Sep. 10, 2020].
Ramlall et aL. Immune complement and coagulation dysfunction in adverse outcomes of SARS-CoV-2 infection. Nat Med 26, 1609-1615 (2020). Published Aug. 3, 2020. https://doi.org/10.1038/s41591-020-1021-2, Sep. 10, 2020 [reference "AA" in IDS filed Sep. 10, 2020].
Partial European search report dated Dec. 21, 2020 issued in European patent application No. 20185556.6.
Mahmudpour M. et al., "COVID-19 cytokine storm: The anger of inflammation", Cytokine, Academic Press Ltd, Philadelphia, PA, US, vol. 133, May 30, 2020 (May 30, 2020), XP086227981, ISSN: 1043-4666, DOI: 10.1016/J.CYTO.2020.155151.
Huber-Lang, M. et al., "Double Blockade of CD14 and Complement C5 Abolishes the Cytokine Storm and Improves Morbidity and Survival in Polymicrobial Sepsis in Mice", The Journal of Immunology, vo. 192, No. 11, Apr. 30, 2014 (Apr. 30, 2014), pp. 5324-5331; XP055758570, US ISSN 0022-1767, DOI: https://doi.org/10.4049.jimmunol.1400341.
Dituri et al. The Interactivity between TGFβ and BMP Signaling in Organogenesis, Fibrosis, and Cancer. *Cells*. 2019;8(10):1130. Published Sep. 23, 2019. doi:10.3390/cells8101130.
Fletcher-Sandersjöö et al. Does Complement-Mediated Hemostatic Disturbance Occur in Traumatic Brain Injury? A Literature Review and Observational Study Protocol. *Int J Mol Sci.* 2020;21(5):1596. Published Feb. 26, 2020. doi:10.3390/ijms21051596.
Kay et al. Distribution, dynamics and functional roles of phosphatidylserine within the cell. *Cell Commun Signal* 17, 126 (2019). Published Oct. 15, 2019 https://doi.org/10.1186/s12964-019-0438-z.
Nagata et al. Flippase and scramblase for phosphatidylserine exposure. Curr Opin Immunol. Feb. 2020;62:31-38. doi: 10.1016/j.coi.2019.11.009. Epub Dec. 11, 2019. PMID: 31837595.
Szebeni et a. Human Clinical Relevance of the Porcine Model of Pseudoallergic Infusion Reactions. *Biomedicines*. 2020;8(4):82. Published Apr. 8, 2020. doi:10.3390/biomedicines8040082.
Vreede et al. Cryptic conspirators: a conversation about thrombocytopenia and antiphospholipid syndrome. Curr Opin Rheumatol. May 2019;31(3):231-240. doi: 10.1097/BOR.0000000000000595. PMID: 30747734; PMCID: PMC6455093.
Waisayarat et al. Intracardiac thrombus in a patient with catastrophic antiphospholipid syndrome: an autopsy case report and review of the literature. *Vasc Health Risk Manag.* 2019;15:253-258. Published Aug. 7, 2019. doi:10.2147/VHRM.S197638.
Ramlall et al. Immune complement and coagulation dysfunction in adverse outcomes of SARS-CoV-2 infection. *Nat Med* 26, 1609-1615 (2020). Published Aug. 3, 2020. https://doi.org/10.1038/s41591-020-1021-2.
"Coronavirus: Hungarian Scientist Develops Medication against Cytokine Storm." MTI—Hungary Today, May 6, 2020. [retrieved on Sep. 13, 2021]. Retrieved from the Internet: <URL: https://hungarytoday.hu/coronavirus-hungarian-scientist-develops-medication-against-cytokine-storm/>.
Farkas et al. C5a receptor expression by TGW neuroblastoma cells. Neuroreport. Sep. 29, 1999;10(14): 3021-3025, Abstract only.
Farkas et al. A neuronal C5a receptor and an associated apoptotic signal transduction pathway. J Physiol. 1998;507 ( Pt 3)(Pt 3):679-687. doi:10.1111/j.1469-7793.1998.679bs.x.
Kaneko et al. Antagonistic peptides against human anaphylatoxin C5a. Immunology vol. 86,1 (1995): 149-54.

* cited by examiner

Fig. 4

3'LTR — Packaging signal — Promoter (EF1α) — Optimized leader peptide — Cleavage site — Recombinant BNP-67 prepropeptein — T->N mutation / Activation site — Enhancer — 5'LTR

Fig. 5

Mean arterial blood pressure (mmHg) vs Time (min.)

- ■ PR226MAP only
- ▲ C5a only
- ▼ PR226MAP+C5a

↑ 1 μg/kg PR226MAP
↑ 40nmol/kg C5a iv

Severity of blood pressure decrease

Severity of bradycardia

Fig. 8A
Fig. 8B
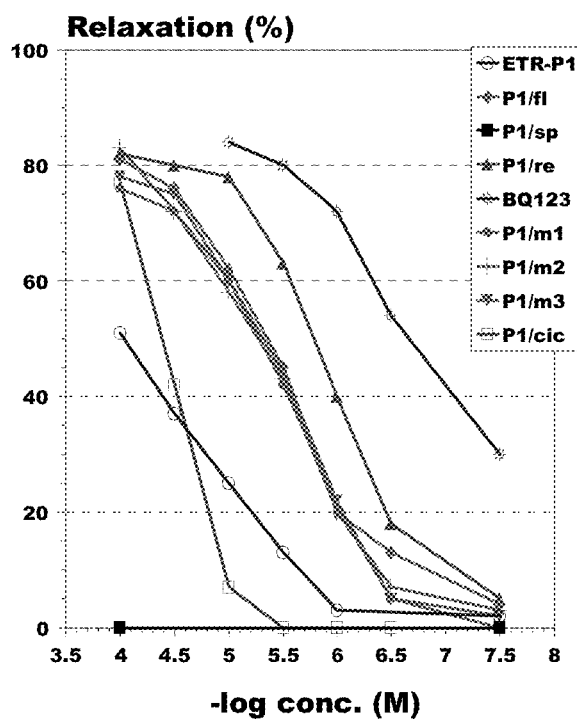
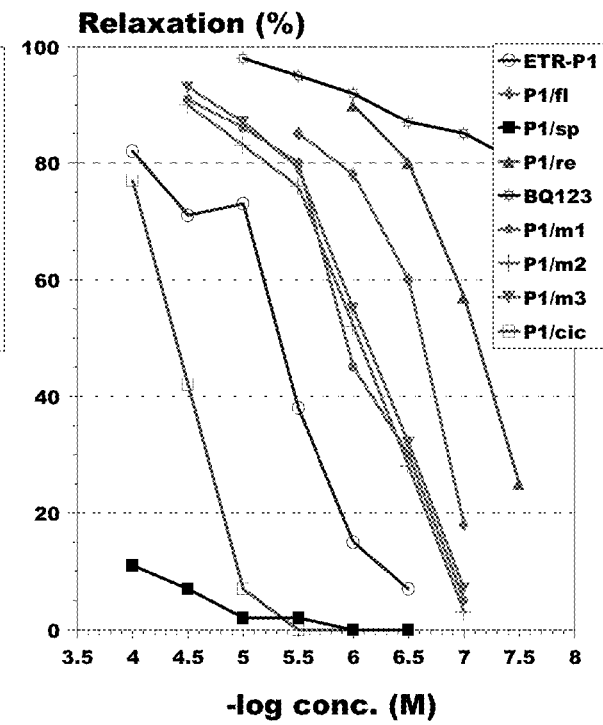

SEQUENCE LISTING

<160> NUMBER OF SEQ ID NOS: 69

<210> SEQ ID NO 1
<211> LENGTH: 10
<212> TYPE: PRT
<213> ORGANISM: Artificial Sequence
<220> FEATURE:
<223> OTHER INFORMATION: Complement factor 3 targeting inhibitor AP1314

<400> SEQUENCE: 1

Ala Pro Asn His Leu Leu Glu Val Arg Val
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Complement factor 3 targeting inhibitor LTA1309

<400> SEQUENCE: 2

Leu Thr Ala Tyr Val Val Lys Val Phe Ser Leu Ala
1               5                   10

<210> SEQ ID NO 3
<211> LENGTH: 14
<212> TYPE: PRT
<213> ORGANISM: Artificial Sequence

```
<220> FEATURE:
<223> OTHER INFORMATION: Complement factor 3 targeting inhibitor DDL1619

<400> SEQUENCE: 3

Asp Asp Leu Lys Gln Leu Ala Asn Gly Val Asp Arg Tyr Ile
1               5                   10

<210> SEQ ID NO 4
<211> LENGTH: 15
<212> TYPE: PRT
<213> ORGANISM: Artificial Sequence
<220> FEATURE:
<223> OTHER INFORMATION: Complement factor 3 targeting inhibitor SDK1606

<400> SEQUENCE: 4

Ser Asp Lys Lys Gly Ile Cys Val Ala Asp Pro Phe Glu Val Thr
1               5                   10                  15

<210> SEQ ID NO 5
<211> LENGTH: 10
<212> TYPE: PRT
<213> ORGANISM: Artificial Sequence
<220> FEATURE:
<223> OTHER INFORMATION: Complement factor 3 targeting inhibitor SDA984

<400> SEQUENCE: 5

Ser Asp Ala Gly Leu Thr Phe Thr Ser Ser
1               5                   10

<210> SEQ ID NO 6
<211> LENGTH: 16
<212> TYPE: PRT
<213> ORGANISM: Artificial Sequence
<220> FEATURE:
<223> OTHER INFORMATION: Complement factor 3 targeting inhibitor SDK1709

<400> SEQUENCE: 6

Ser Asp Lys Lys Gly Ile Cys Val Ala Asp Pro Cys Phe Glu Val Thr
1               5                   10                  15

<210> SEQ ID NO 7
<211> LENGTH: 17
<212> TYPE: PRT
<213> ORGANISM: Artificial Sequence
<220> FEATURE:
<223> OTHER INFORMATION: Complement factor 3 targeting inhibitor VQA1857

<400> SEQUENCE: 7

Val Gln Ala Glu Arg Ser Gly Ile Pro Ile Val Thr Ser Pro Tyr Gln
1               5                   10                  15

Ile

<210> SEQ ID NO 8
<211> LENGTH: 13
<212> TYPE: PRT
<213> ORGANISM: Artificial Sequence
<220> FEATURE:
<223> OTHER INFORMATION: Complement factor 3 targeting inhibitor QAL1363

<400> SEQUENCE: 8

Gln Ala Leu Pro Tyr Ser Thr Val Gly Asn Ser Asn Leu
1               5                   10

<210> SEQ ID NO 9
<211> LENGTH: 12
<212> TYPE: PRT
```

```
<213> ORGANISM: Artificial Sequence
<220> FEATURE:
<223> OTHER INFORMATION: Complement factor 3 targeting inhibitor NIF1464

<400> SEQUENCE: 9

Asn Ile Phe Leu Lys Asp Ser Ile Thr Thr Trp Glu
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Complement factor 3 targeting inhibitor LHL1431

<400> SEQUENCE: 10

Leu His Leu Ser Val Arg Thr Leu Glu Leu Arg Pro
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Complement factor 3 targeting inhibitor QRS1008

<400> SEQUENCE: 11

Gln Arg Ser Tyr Thr Val Ala Ile Ala
1               5

<210> SEQ ID NO 12
<211> LENGTH: 9
<212> TYPE: PRT
<213> ORGANISM: Artificial Sequence
<220> FEATURE:
<223> OTHER INFORMATION: Complement factor 3 targeting inhibitor KRP1057

<400> SEQUENCE: 12

Lys Arg Pro Gln Asp Ala Lys Asn Thr
1               5

<210> SEQ ID NO 13
<211> LENGTH: 9
<212> TYPE: PRT
<213> ORGANISM: Artificial Sequence
<220> FEATURE:
<223> OTHER INFORMATION: Complement factor 3 targeting inhibitor ERL1041

<400> SEQUENCE: 13

Glu Arg Leu Gly Arg Glu Gly Val Gln
1               5

<210> SEQ ID NO 14
<211> LENGTH: 14
<212> TYPE: PRT
<213> ORGANISM: Artificial Sequence
<220> FEATURE:
<223> OTHER INFORMATION: Complement factor 3 targeting inhibitor LNC1538

<400> SEQUENCE: 14

Leu Asn Cys Gln Arg Tyr Tyr Gly Gly Gly Gly Tyr Ser Thr
1               5                   10

<210> SEQ ID NO 15
<211> LENGTH: 10
<212> TYPE: PRT
<213> ORGANISM: Artificial Sequence
```

```
<220> FEATURE:
<223> OTHER INFORMATION: Complement factor 3 targeting inhibitor LSR1099

<400> SEQUENCE: 15

Leu Ser Arg Lys Val Leu Leu Asp Gly Val
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Complement factor 3 targeting inhibitor ESA1331

<400> SEQUENCE: 16

Glu Ser Ala Ser Leu Arg Ser Glu Glu Thr Lys Val
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Complement factor 3 targeting inhibitor GQW1513

<400> SEQUENCE: 17

Gly Gln Trp Lys Ile Arg Ala Tyr Tyr Glu Asn Ser
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Complement factor 3 targeting inhibitor IAV1501

<400> SEQUENCE: 18

Ile Ala Val His Tyr Leu Asp Glu Thr Glu Gln Trp
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Complement factor 3 targeting inhibitor LRL1384

<400> SEQUENCE: 19

Leu Arg Leu Pro Tyr Val Val Arg Glu Gln Leu
1               5                   10

<210> SEQ ID NO 20
<211> LENGTH: 13
<212> TYPE: PRT
<213> ORGANISM: Artificial Sequence
<220> FEATURE:
<223> OTHER INFORMATION: Complement factor 3 targeting inhibitor TAY1409

<400> SEQUENCE: 20

Thr Ala Tyr Val Val Lys Val Phe Ser Leu Ala Val Asn
1               5                   10

<210> SEQ ID NO 21
<211> LENGTH: 423
<212> TYPE: PRT
<213> ORGANISM: Artificial Sequence
```

<220> FEATURE:
<223> OTHER INFORMATION: CPB1 human carboxypeptidase B

<400> SEQUENCE: 21

```
Met Arg Ala Pro Ala Gln Ile Phe Gly Phe Leu Leu Leu Phe Pro
1               5                   10                  15

Gly Thr Cys Phe Ala His His Gly Gly Glu His Phe Glu Gly Lys
                20                  25                  30

Val Phe Arg Val Asn Val Glu Asp Glu Asn His Ile Asn Ile Arg
            35                  40                  45

Glu Leu Ala Ser Thr Thr Gln Ile Asp Phe Trp Lys Pro Asp Ser Val
50                  55                  60

Thr Gln Ile Lys Pro His Ser Thr Val Asp Phe Arg Val Lys Ala Glu
65                  70                  75                  80

Asp Thr Val Thr Val Glu Asn Val Leu Lys Gln Asn Glu Leu Gln Tyr
                85                  90                  95

Lys Val Leu Ile Ser Asn Leu Arg Asn Val Val Glu Ala Gln Phe Asp
                100                 105                 110

Ser Arg Val Arg Ala Asn Gly His Ser Tyr Glu Lys Tyr Asn Lys Trp
            115                 120                 125

Glu Thr Ile Glu Ala Trp Thr Gln Gln Val Ala Thr Glu Asn Pro Ala
130                 135                 140

Leu Ile Ser Arg Ser Val Ile Gly Thr Thr Phe Glu Gly Arg Ala Ile
145                 150                 155                 160

Tyr Leu Leu Lys Val Gly Lys Ala Gly Gln Asn Lys Pro Ala Ile Phe
                165                 170                 175

Met Asp Cys Gly Phe His Ala Arg Glu Trp Ile Ser Pro Ala Phe Cys
            180                 185                 190

Gln Trp Phe Val Arg Glu Ala Val Arg Thr Tyr Gly Arg Glu Ile Gln
            195                 200                 205

Val Thr Glu Leu Leu Asp Lys Leu Asp Phe Tyr Val Leu Pro Val Leu
210                 215                 220

Asn Ile Asp Gly Tyr Ile Tyr Thr Trp Thr Lys Ser Arg Phe Trp Arg
225                 230                 235                 240

Lys Thr Arg Ser Thr His Thr Gly Ser Ser Cys Ile Gly Thr Asp Pro
                245                 250                 255

Asn Arg Asn Phe Asp Ala Gly Trp Cys Glu Ile Gly Ala Ser Arg Asn
            260                 265                 270

Pro Cys Asp Glu Thr Tyr Cys Gly Pro Ala Ala Glu Ser Glu Lys Glu
            275                 280                 285

Thr Lys Ala Leu Ala Asp Phe Ile Arg Asn Lys Leu Ser Ser Ile Lys
290                 295                 300

Ala Tyr Leu Thr Ile His Ser Tyr Ser Gln Met Met Ile Tyr Pro Tyr
305                 310                 315                 320

Ser Tyr Ala Tyr Lys Leu Gly Glu Asn Asn Ala Glu Leu Asn Ala Leu
                325                 330                 335

Ala Lys Ala Thr Val Lys Glu Leu Ala Ser Leu His Gly Thr Lys Tyr
            340                 345                 350

Thr Tyr Gly Pro Gly Ala Thr Thr Ile Tyr Pro Ala Ala Gly Gly Ser
            355                 360                 365

Asp Asp Trp Ala Tyr Asp Gln Gly Ile Arg Tyr Ser Phe Thr Phe Glu
370                 375                 380

Leu Arg Asp Thr Gly Arg Tyr Gly Phe Leu Leu Pro Glu Ser Gln Ile
385                 390                 395                 400
```

```
Arg Ala Thr Cys Glu Glu Thr Phe Leu Ala Ile Lys Tyr Val Ala Ser
                405                 410                 415

Tyr Val Leu Glu His Leu Tyr
            420

<210> SEQ ID NO 22
<211> LENGTH: 422
<212> TYPE: PRT
<213> ORGANISM: Artificial Sequence
<220> FEATURE:
<223> OTHER INFORMATION: CPB2 human carboxypeptidase B2, TAFI

<400> SEQUENCE: 22

Met Arg Ala Pro Ala Gln Ile Phe Gly Phe Leu Leu Leu Leu Phe Pro
1               5                   10                  15

Gly Thr Cys Phe Ala Phe Gln Ser Gly Gln Val Leu Ala Ala Leu Pro
            20                  25                  30

Arg Thr Ser Arg Gln Val Gln Val Leu Gln Asn Leu Thr Thr Thr Tyr
        35                  40                  45

Glu Ile Val Leu Trp Gln Pro Val Thr Ala Asp Leu Ile Val Lys Lys
    50                  55                  60

Lys Gln Val His Phe Phe Val Asn Ala Ser Asp Val Asp Asn Val Lys
65                  70                  75                  80

Ala His Leu Asn Val Ser Gly Ile Pro Cys Ser Val Leu Leu Ala Asp
                85                  90                  95

Val Glu Asp Leu Ile Gln Gln Gln Ile Ser Asn Asp Thr Val Ser Gly
            100                 105                 110

Arg Ala Ser Ala Ser Tyr Tyr Glu Gln Tyr His Ser Leu Asn Glu Ile
        115                 120                 125

Tyr Ser Trp Ile Glu Phe Ile Thr Glu Arg His Pro Asp Met Leu Thr
    130                 135                 140

Lys Ile His Ile Gly Ser Ser Phe Glu Lys Tyr Pro Leu Tyr Val Leu
145                 150                 155                 160

Lys Val Ser Gly Lys Glu Gln Thr Ala Lys Asn Ala Ile Trp Ile Asp
                165                 170                 175

Cys Gly Ile His Ala Arg Glu Trp Ile Ser Pro Ala Phe Cys Leu Trp
            180                 185                 190

Phe Ile Gly His Ile Thr Gln Phe Tyr Gly Ile Ile Gly Gln Tyr Thr
        195                 200                 205

Asn Leu Leu Arg Leu Val Asp Phe Tyr Val Met Pro Val Val Asn Val
    210                 215                 220

Asp Gly Tyr Asp Tyr Ser Trp Lys Lys Asn Arg Met Trp Arg Lys Asn
225                 230                 235                 240

Arg Ser Phe Tyr Ala Asn Asn His Cys Ile Gly Thr Asp Leu Asn Arg
                245                 250                 255

Asn Phe Ala Ser Lys His Trp Cys Glu Glu Gly Ala Ser Ser Ser Ser
            260                 265                 270

Cys Ser Glu Thr Tyr Cys Gly Leu Tyr Pro Glu Ser Glu Pro Glu Val
        275                 280                 285

Lys Ala Val Ala Ser Phe Leu Arg Arg Asn Ile Asn Gln Ile Lys Ala
    290                 295                 300

Tyr Ile Ser Met His Ser Tyr Ser Gln His Ile Val Phe Pro Tyr Ser
305                 310                 315                 320

Tyr Thr Arg Ala Lys Ser Lys Asp His Glu Glu Leu Ser Leu Val Ala
                325                 330                 335
```

```
Ser Glu Ala Val Arg Ala Ile Glu Lys Thr Ser Lys Asn Thr Arg Tyr
        340                 345                 350

Thr His Gly His Gly Ser Glu Thr Leu Tyr Leu Ala Pro Gly Gly Gly
        355                 360                 365

Asp Asp Trp Ile Tyr Asp Leu Gly Ile Lys Tyr Ser Phe Thr Ile Glu
        370                 375                 380

Leu Arg Asp Thr Gly Thr Tyr Gly Phe Leu Leu Pro Glu Arg Tyr Ile
385                 390                 395                 400

Lys Pro Thr Cys Arg Glu Ala Phe Ala Ala Val Ser Lys Ile Ala Trp
                405                 410                 415

His Val Ile Arg Asn Val
            420

<210> SEQ ID NO 23
<211> LENGTH: 18
<212> TYPE: PRT
<213> ORGANISM: Artificial Sequence
<220> FEATURE:
<223> OTHER INFORMATION: Complement factor 5a receptor targeting
      inhibitor LRT2463

<400> SEQUENCE: 23

Leu Arg Thr Trp Ser Arg Arg Ala Thr Arg Ser Thr Lys Thr Leu Lys
1               5                   10                  15

Val Val

<210> SEQ ID NO 24
<211> LENGTH: 21
<212> TYPE: PRT
<213> ORGANISM: Artificial Sequence
<220> FEATURE:
<223> OTHER INFORMATION: Complement factor 5a receptor targeting
      inhibitor LRT10353
<220> FEATURE:
<221> NAME/KEY: MISC_FEATURE
<222> LOCATION: (1)..(21)
<223> OTHER INFORMATION: This sequence is part of a branched peptide.
<220> FEATURE:
<221> NAME/KEY: SITE
<222> LOCATION: (19)..(20)
<223> OTHER INFORMATION: Sites of linkage in tetrameric dendromer

<400> SEQUENCE: 24

Leu Arg Thr Trp Ser Arg Arg Ala Thr Arg Ser Thr Lys Thr Leu Lys
1               5                   10                  15

Val Val Lys Lys Val
            20

<210> SEQ ID NO 25
<211> LENGTH: 22
<212> TYPE: PRT
<213> ORGANISM: Artificial Sequence
<220> FEATURE:
<223> OTHER INFORMATION: Complement factor 5a receptor targeting
      inhibitor LRT20707
<220> FEATURE:
<221> NAME/KEY: MISC_FEATURE
<222> LOCATION: (1)..(22)
<223> OTHER INFORMATION: This sequence is part of a branched peptide.
<220> FEATURE:
<221> NAME/KEY: SITE
<222> LOCATION: (19)..(21)
<223> OTHER INFORMATION: Sites of linkage in octameric dendromer
```

```
<400> SEQUENCE: 25

Leu Arg Thr Trp Ser Arg Arg Ala Thr Arg Ser Thr Lys Thr Leu Lys
1               5                   10                  15

Val Val Lys Lys Lys Val
            20

<210> SEQ ID NO 26
<211> LENGTH: 18
<212> TYPE: PRT
<213> ORGANISM: Artificial Sequence
<220> FEATURE:
<223> OTHER INFORMATION: Complement factor 5a receptor targeting
      inhibitor DYG2094

<400> SEQUENCE: 26

Asp Tyr Gly His Tyr Asp Asp Lys Asp Thr Leu Asp Leu Asn Thr Pro
1               5                   10                  15

Val Asp

<210> SEQ ID NO 27
<211> LENGTH: 16
<212> TYPE: PRT
<213> ORGANISM: Artificial Sequence
<220> FEATURE:
<223> OTHER INFORMATION: Complement factor 5a receptor targeting
      inhibitor HWP1667

<400> SEQUENCE: 27

His Trp Pro Phe Gly Gly Ala Ala Cys Ser Ile Leu Pro Ser Leu Ile
1               5                   10                  15

<210> SEQ ID NO 28
<211> LENGTH: 14
<212> TYPE: PRT
<213> ORGANISM: Artificial Sequence
<220> FEATURE:
<223> OTHER INFORMATION: Endothelin A receptor targeting inhibitor
      CAL1595

<400> SEQUENCE: 28

Cys Ala Leu Ser Val Asp Arg Tyr Arg Ala Val Ala Ser Trp
1               5                   10

<210> SEQ ID NO 29
<211> LENGTH: 15
<212> TYPE: PRT
<213> ORGANISM: Artificial Sequence
<220> FEATURE:
<223> OTHER INFORMATION: Endothelin A receptor targeting inhibitor
      CAL1698

<400> SEQUENCE: 29

Cys Ala Leu Ser Val Asp Arg Tyr Arg Ala Val Ala Ser Trp Cys
1               5                   10                  15

<210> SEQ ID NO 30
<211> LENGTH: 16
<212> TYPE: PRT
<213> ORGANISM: Artificial Sequence
<220> FEATURE:
<223> OTHER INFORMATION: Endothelin A receptor targeting inhibitor
      QGI10797
<220> FEATURE:
<221> NAME/KEY: MISC_FEATURE
<222> LOCATION: (1)..(16)
<223> OTHER INFORMATION: This sequence is part of a branched peptide.
```

```
<220> FEATURE:
<221> NAME/KEY: SITE
<222> LOCATION: (13)..(15)
<223> OTHER INFORMATION: Sites of linkage in octameric dendromer

<400> SEQUENCE: 30

Gln Gly Ile Gly Ile Pro Leu Ile Thr Ala Glu Ile Lys Lys Lys Val
1               5                   10                  15

<210> SEQ ID NO 31
<211> LENGTH: 21
<212> TYPE: PRT
<213> ORGANISM: Artificial Sequence
<220> FEATURE:
<223> OTHER INFORMATION: Endothelin A receptor targeting inhibitor
      LNL2390

<400> SEQUENCE: 31

Leu Asn Leu Cys Ala Leu Ser Val Asp Arg Tyr Arg Ala Val Ala Ser
1               5                   10                  15

Trp Ser Arg Val Ile
            20

<210> SEQ ID NO 32
<211> LENGTH: 21
<212> TYPE: PRT
<213> ORGANISM: Artificial Sequence
<220> FEATURE:
<223> OTHER INFORMATION: Endothelin A receptor targeting inhibitor
      IVR2333

<400> SEQUENCE: 32

Ile Val Arg Ser Trp Ser Ala Val Ala Arg Tyr Asp Ser Val Leu Ala
1               5                   10                  15

Cys Leu Asn Leu Val
            20

<210> SEQ ID NO 33
<211> LENGTH: 24
<212> TYPE: PRT
<213> ORGANISM: Artificial Sequence
<220> FEATURE:
<223> OTHER INFORMATION: Endothelin A receptor targeting inhibitor
      CAL2614

<400> SEQUENCE: 33

Cys Ala Leu Ser Val Asp Arg Tyr Arg Ala Val Ala Ser Trp Gly Ile
1               5                   10                  15

Pro Leu Ile Thr Ala Ile Glu Ile
            20

<210> SEQ ID NO 34
<211> LENGTH: 22
<212> TYPE: PRT
<213> ORGANISM: Artificial Sequence
<220> FEATURE:
<223> OTHER INFORMATION: Endothelin A receptor targeting inhibitor
      VLN2390

<400> SEQUENCE: 34

Val Leu Asn Leu Cys Ala Leu Ser Val Asp Arg Tyr Gly Ala Val Ala
1               5                   10                  15

Ser Trp Ser Arg Val Ile
            20
```

```
<210> SEQ ID NO 35
<211> LENGTH: 22
<212> TYPE: PRT
<213> ORGANISM: Artificial Sequence
<220> FEATURE:
<223> OTHER INFORMATION: Endothelin A receptor targeting inhibitor
      VLN2433

<400> SEQUENCE: 35

Val Leu Asn Leu Cys Ala Gly Ser Val Asp Arg Tyr Arg Ala Val Ala
1               5                   10                  15

Ser Trp Ser Arg Val Ile
            20

<210> SEQ ID NO 36
<211> LENGTH: 22
<212> TYPE: PRT
<213> ORGANISM: Artificial Sequence
<220> FEATURE:
<223> OTHER INFORMATION: Endothelin A receptor targeting inhibitor
      VLN2443

<400> SEQUENCE: 36

Val Leu Asn Leu Gly Ala Leu Ser Val Asp Arg Tyr Arg Ala Val Ala
1               5                   10                  15

Ser Trp Ser Arg Val Ile
            20

<210> SEQ ID NO 37
<211> LENGTH: 5
<212> TYPE: PRT
<213> ORGANISM: Artificial Sequence
<220> FEATURE:
<223> OTHER INFORMATION: Amino acid residue of endothelin A receptor
      targeting inhibitor TDP610
<220> FEATURE:
<221> NAME/KEY: SITE
<222> LOCATION: (1)..(1)
<223> OTHER INFORMATION: D-tryptamine
<220> FEATURE:
<221> NAME/KEY: REGION
<222> LOCATION: (1)..(5)
<223> OTHER INFORMATION: Cyclic peptide
<220> FEATURE:
<221> NAME/KEY: SITE
<222> LOCATION: (2)..(2)
<223> OTHER INFORMATION: D-aspartic acid
<220> FEATURE:
<221> NAME/KEY: SITE
<222> LOCATION: (4)..(4)
<223> OTHER INFORMATION: D-valine

<400> SEQUENCE: 37

Xaa Asp Pro Val Leu
1               5

<210> SEQ ID NO 38
<211> LENGTH: 508
<212> TYPE: PRT
<213> ORGANISM: Artificial Sequence
<220> FEATURE:
<223> OTHER INFORMATION: Recombinant human bone morphogenic protein BMP
      6

<400> SEQUENCE: 38

Met Pro Gly Leu Gly Arg Arg Ala Gln Trp Leu Cys Trp Trp Trp Gly
1               5                   10                  15

Leu Leu Cys Ser Cys Cys Gly Pro Pro Pro Leu Arg Pro Pro Leu Pro
            20                  25                  30
```

```
Ala Ala Ala Ala Ala Ala Gly Gln Leu Leu Gly Asp Gly
            35                  40                  45

Ser Pro Gly Arg Thr Glu Gln Pro Pro Ser Pro Gln Ser Ser Ser
 50                  55                  60

Gly Phe Leu Tyr Arg Arg Leu Lys Thr Gln Glu Lys Arg Glu Met Gln
 65                  70                  75                  80

Lys Glu Ile Leu Ser Val Leu Gly Leu Pro His Arg Pro Arg Pro Leu
                 85                  90                  95

His Gly Leu Gln Gln Pro Gln Pro Ala Leu Arg Gln Glu Glu
                100                 105                 110

Gln Gln Gln Gln Gln Gln Leu Pro Arg Gly Glu Pro Pro Gly Arg
            115                 120                 125

Leu Lys Ser Ala Pro Leu Phe Met Leu Asp Leu Tyr Asn Ala Leu Ser
        130                 135                 140

Ala Asp Asn Asp Glu Asp Gly Ala Ser Glu Gly Glu Arg Gln Gln Ser
145                 150                 155                 160

Trp Pro His Glu Ala Ala Ser Ser Gln Arg Arg Gln Pro Pro
                165                 170                 175

Gly Ala Ala His Pro Leu Asn Arg Lys Ser Leu Leu Ala Pro Gly Ser
                180                 185                 190

Gly Ser Gly Gly Ala Ser Pro Leu Thr Ser Ala Gln Asp Ser Ala Phe
        195                 200                 205

Leu Asn Asp Ala Asp Met Val Met Ser Phe Val Asn Leu Val Glu Tyr
        210                 215                 220

Asp Lys Glu Phe Ser Pro Arg Gln Arg His His Lys Glu Phe Lys Phe
225                 230                 235                 240

Asn Leu Ser Gln Ile Pro Glu Gly Glu Val Val Thr Ala Ala Glu Phe
                245                 250                 255

Arg Ile Tyr Lys Asp Cys Val Met Gly Ser Phe Lys Asn Gln Thr Phe
                260                 265                 270

Leu Ile Ser Ile Tyr Gln Val Leu Gln Glu His Gln His Arg Asp Ser
        275                 280                 285

Asp Leu Phe Leu Leu Asp Thr Arg Val Val Trp Ala Ser Glu Glu Gly
        290                 295                 300

Trp Leu Glu Phe Asp Ile Thr Ala Thr Ser Asn Leu Trp Val Val Thr
305                 310                 315                 320

Pro Gln His Asn Met Gly Leu Gln Leu Ser Val Val Thr Arg Asp Gly
                325                 330                 335

Val His Val His Pro Arg Ala Ala Gly Leu Val Gly Arg Asp Gly Pro
                340                 345                 350

Tyr Asp Lys Gln Pro Phe Met Val Ala Phe Lys Val Ser Glu Val
        355                 360                 365

His Val Arg Thr Thr Arg Ser Ala Ser Ser Arg Arg Gln Ala Ser
        370                 375                 380

Arg Asn Arg Ser Thr Gln Ser Gln Asp Val Ala Arg Val Ser Ser Ala
385                 390                 395                 400

Ser Asp Tyr Asn Ser Ser Glu Leu Lys Thr Ala Cys Arg Lys His Glu
                405                 410                 415

Leu Tyr Val Ser Phe Gln Asp Leu Gly Trp Gln Asp Trp Ile Ile Ala
        420                 425                 430

Pro Lys Gly Tyr Ala Ala Asn Tyr Cys Asp Gly Glu Cys Ser Phe Pro
        435                 440                 445
```

```
Leu Asn Ala His Met Asn Ala Thr Asn His Ala Ile Val Gln Thr Leu
        450                 455                 460

Val His Leu Met Asn Pro Glu Tyr Val Pro Lys Pro Cys Cys Ala Pro
465                 470                 475                 480

Thr Lys Leu Asn Ala Ile Ser Val Leu Tyr Phe Asp Asp Asn Ser Asn
                485                 490                 495

Val Ile Leu Lys Lys Tyr Arg Asn Met Val Val Arg
                500                 505

<210> SEQ ID NO 39
<211> LENGTH: 514
<212> TYPE: PRT
<213> ORGANISM: Artificial Sequence
<220> FEATURE:
<223> OTHER INFORMATION: Recombinant bone morphogenic protein BMP 6/7
      for secretory production

<400> SEQUENCE: 39

Met Arg Ala Pro Ala Gln Ile Phe Gly Phe Leu Leu Leu Leu Phe Pro
1               5                   10                  15

Gly Thr Cys Phe Ala Cys Cys Gly Pro Pro Leu Arg Pro Pro Leu
            20                  25                  30

Pro Ala Ala Ala Ala Ala Ala Gly Gly Gln Leu Leu Gly Asp Gly
            35                  40                  45

Gly Ser Pro Gly Arg Thr Glu Gln Pro Pro Ser Pro Gln Ser Ser
50                  55                  60

Ser Gly Phe Leu Tyr Arg Arg Leu Lys Thr Gln Glu Lys Arg Glu Met
65                  70                  75                  80

Gln Lys Glu Ile Leu Ser Val Leu Gly Leu Pro His Arg Pro Arg Pro
                85                  90                  95

Leu His Gly Leu Gln Gln Pro Gln Pro Pro Ala Leu Arg Gln Gln Glu
                100                 105                 110

Glu Gln Gln Gln Gln Gln Gln Leu Pro Arg Gly Glu Pro Pro Pro Gly
                115                 120                 125

Arg Leu Lys Ser Ala Pro Leu Phe Met Leu Asp Leu Tyr Asn Ala Leu
130                 135                 140

Ser Ala Asp Asn Asp Glu Asp Gly Ala Ser Glu Gly Glu Arg Gln Gln
145                 150                 155                 160

Ser Trp Pro His Glu Ala Ala Ser Ser Ser Gln Arg Arg Gln Pro Pro
                165                 170                 175

Pro Gly Ala Ala His Pro Leu Asn Arg Lys Ser Leu Leu Ala Pro Gly
                180                 185                 190

Ser Gly Ser Gly Gly Ala Ser Pro Leu Thr Ser Ala Gln Asp Ser Ala
                195                 200                 205

Phe Leu Asn Asp Ala Asp Met Val Met Ser Phe Val Asn Leu Val Glu
210                 215                 220

Tyr Asp Lys Glu Phe Ser Pro Arg Gln Arg His His Lys Glu Phe Lys
225                 230                 235                 240

Phe Asn Leu Ser Gln Ile Pro Glu Gly Glu Val Val Thr Ala Ala Glu
                245                 250                 255

Phe Arg Ile Tyr Lys Asp Cys Val Met Gly Ser Phe Lys Asn Gln Thr
                260                 265                 270

Phe Leu Ile Ser Ile Tyr Gln Val Leu Gln Glu His Gln His Arg Asp
                275                 280                 285

Ser Asp Leu Phe Leu Leu Asp Thr Arg Val Val Trp Ala Ser Glu Glu
                290                 295                 300
```

```
Gly Trp Leu Glu Phe Asp Ile Thr Ala Thr Ser Asn Leu Trp Val Val
305                 310                 315                 320

Thr Pro Gln His Asn Met Gly Leu Gln Leu Ser Val Val Thr Arg Asp
                325                 330                 335

Gly Val His Val His Pro Arg Ala Ala Gly Leu Val Gly Arg Asp Gly
            340                 345                 350

Pro Tyr Asp Lys Gln Pro Phe Met Val Ala Phe Phe Lys Val Ser Glu
                355                 360                 365

Val His Val Arg Thr Thr Arg Ser Ala Ser Ser Arg Arg Gln Gln
            370                 375                 380

Ser Arg Asn Arg Ser Thr Gln Ser Gln Asp Val Ala Arg Val Ser Ser
385                 390                 395                 400

Ala Ser Asp Tyr Asn Ser Ser Glu Leu Lys Thr Ala Cys Arg Lys His
                405                 410                 415

Glu Leu Tyr Val Ser Phe Gln Asp Leu Gly Trp Gln Asp Trp Ile Ile
                420                 425                 430

Ala Pro Lys Gly Tyr Ala Ala Asn Tyr Cys Asp Gly Glu Cys Ser Phe
                435                 440                 445

Pro Leu Asn Ala His Met Asn Ala Thr Asn His Ala Ile Val Gln Thr
450                 455                 460

Leu Val His Leu Met Asn Pro Glu Tyr Val Pro Lys Pro Cys Cys Ala
465                 470                 475                 480

Pro Thr Lys Leu Asn Ala Ile Ser Val Leu Tyr Phe Asp Asp Asn Ser
                485                 490                 495

Asn Val Ile Leu Lys Lys Tyr Arg Asn Met Val Val Arg Ala Cys Gly
                500                 505                 510

Cys His

<210> SEQ ID NO 40
<211> LENGTH: 309
<212> TYPE: PRT
<213> ORGANISM: Artificial Sequence
<220> FEATURE:
<223> OTHER INFORMATION: Recombinant bone morphogenic protein BMP 6/7
      for cell surface and exosome expression

<400> SEQUENCE: 40

Met Arg Ala Pro Ala Gln Ile Phe Gly Phe Leu Leu Leu Leu Phe Pro
1               5                   10                  15

Gly Thr Cys Phe Ala Gln Gln Ser Arg Asn Arg Ser Thr Gln Ser Gln
                20                  25                  30

Asp Val Ala Arg Val Ser Ser Ala Ser Asp Tyr Asn Ser Ser Glu Leu
                35                  40                  45

Lys Thr Ala Cys Arg Lys His Glu Leu Tyr Val Ser Phe Gln Asp Leu
            50                  55                  60

Gly Trp Gln Asp Trp Ile Ile Ala Pro Lys Gly Tyr Ala Ala Asn Tyr
65                  70                  75                  80

Cys Asp Gly Glu Cys Ser Phe Pro Leu Asn Ala His Met Asn Ala Thr
                85                  90                  95

Asn His Ala Ile Val Gln Thr Leu Val His Leu Met Asn Pro Glu Tyr
                100                 105                 110

Val Pro Lys Pro Cys Cys Ala Pro Thr Lys Leu Asn Ala Ile Ser Val
            115                 120                 125

Leu Tyr Phe Asp Asp Asn Ser Asn Val Ile Leu Lys Lys Tyr Arg Asn
130                 135                 140
```

```
Met Val Val Arg Ala Cys Gly Cys His Arg Trp Pro Glu Ser Pro Lys
145                 150                 155                 160

Ala Gln Ala Ser Ser Val Pro Thr Ala Gln Pro Gln Ala Glu Gly Ser
            165                 170                 175

Leu Ala Lys Ala Thr Ala Pro Ala Thr Thr Arg Asn Thr Gly Arg Gly
            180                 185                 190

Gly Glu Glu Lys Lys Lys Glu Lys Glu Lys Glu Gln Glu Glu Arg
        195                 200                 205

Glu Thr Lys Thr Pro Glu Cys Pro Gln Cys Tyr Asn Cys Pro Asn Pro
    210                 215                 220

Thr Ala Asp Cys Lys Thr Ala Val Asn Cys Ser Ser Asp Phe Asp Ala
225                 230                 235                 240

Cys Leu Ile Thr Lys Ala Glu Leu Gly Tyr His Tyr Val Ala Gln Ala
            245                 250                 255

Gly Arg Arg Gln Ser Ser His Phe Ser Leu Leu Lys Cys Trp Asp Tyr
            260                 265                 270

Arg Cys Glu Pro Ser His Trp Pro His Cys Pro Tyr Phe Asn Trp Gly
            275                 280                 285

Tyr Lys Cys Ile Thr Ser Val Gly Ser Leu Ser Ile Ala Ile Ser Thr
290                 295                 300

Thr Ser Gln Pro Ala
305

<210> SEQ ID NO 41
<211> LENGTH: 361
<212> TYPE: PRT
<213> ORGANISM: Artificial Sequence
<220> FEATURE:
<223> OTHER INFORMATION: Recombinant BMP7 active domain I with inserts
      from BMP6

<400> SEQUENCE: 41

Cys Cys Gly Pro Pro Leu Arg Pro Leu Pro Ala Ala Ala Ala Ala
1               5                   10                  15

Ala Ala Ala Gly Gly Gln Leu Leu Gly Asp Gly Gly Ser Pro Gly Arg
            20                  25                  30

Thr Glu Gln Pro Pro Ser Pro Gln Ser Ser Ser Gly Phe Leu Tyr
        35                  40                  45

Arg Arg Leu Lys Thr Gln Glu Lys Arg Glu Met Gln Lys Glu Ile Leu
    50                  55                  60

Ser Val Leu Gly Leu Pro His Arg Pro Arg Pro Leu His Gly Leu Gln
65                  70                  75                  80

Gln Pro Gln Pro Pro Ala Leu Arg Gln Gln Glu Glu Gln Gln Gln Gln
                85                  90                  95

Gln Gln Leu Pro Arg Gly Glu Pro Pro Gly Arg Leu Lys Ser Ala
            100                 105                 110

Pro Leu Phe Met Leu Asp Leu Tyr Asn Ala Leu Ser Ala Asp Asn Asp
            115                 120                 125

Glu Asp Gly Ala Ser Glu Gly Glu Arg Gln Gln Ser Trp Pro His Glu
130                 135                 140

Ala Ala Ser Ser Ser Gln Arg Arg Gln Pro Pro Pro Gly Ala Ala His
145                 150                 155                 160

Pro Leu Asn Arg Lys Ser Leu Leu Ala Pro Gly Ser Gly Ser Gly Gly
            165                 170                 175

Ala Ser Pro Leu Thr Ser Ala Gln Asp Ser Ala Phe Leu Asn Asp Ala
            180                 185                 190
```

```
Asp Met Val Met Ser Phe Val Asn Leu Val Glu Tyr Asp Lys Glu Phe
        195                 200                 205
Ser Pro Arg Gln Arg His His Lys Glu Phe Lys Phe Asn Leu Ser Gln
    210                 215                 220
Ile Pro Glu Gly Glu Val Val Thr Ala Ala Glu Phe Arg Ile Tyr Lys
225                 230                 235                 240
Asp Cys Val Met Gly Ser Phe Lys Asn Gln Thr Phe Leu Ile Ser Ile
            245                 250                 255
Tyr Gln Val Leu Gln Glu His Gln His Arg Asp Ser Asp Leu Phe Leu
                260                 265                 270
Leu Asp Thr Arg Val Val Trp Ala Ser Glu Glu Gly Trp Leu Glu Phe
            275                 280                 285
Asp Ile Thr Ala Thr Ser Asn Leu Trp Val Val Thr Pro Gln His Asn
        290                 295                 300
Met Gly Leu Gln Leu Ser Val Val Thr Arg Asp Gly Val His Val His
305                 310                 315                 320
Pro Arg Ala Ala Gly Leu Val Gly Arg Asp Gly Pro Tyr Asp Lys Gln
                325                 330                 335
Pro Phe Met Val Ala Phe Phe Lys Val Ser Glu Val His Val Arg Thr
            340                 345                 350
Thr Arg Ser Ala Ser Arg Arg Arg
        355                 360

<210> SEQ ID NO 42
<211> LENGTH: 132
<212> TYPE: PRT
<213> ORGANISM: Artificial Sequence
<220> FEATURE:
<223> OTHER INFORMATION: Recombinant BMP7 active domain II with inserts
      from BMP6

<400> SEQUENCE: 42

Gln Gln Ser Arg Asn Arg Ser Thr Gln Ser Gln Asp Val Ala Arg Val
1               5                   10                  15
Ser Ser Ala Ser Asp Tyr Asn Ser Ser Glu Leu Lys Thr Ala Cys Arg
            20                  25                  30
Lys His Glu Leu Tyr Val Ser Phe Gln Asp Leu Gly Trp Gln Asp Trp
        35                  40                  45
Ile Ile Ala Pro Lys Gly Tyr Ala Ala Asn Tyr Cys Asp Gly Glu Cys
    50                  55                  60
Ser Phe Pro Leu Asn Ala His Met Asn Ala Thr Asn His Ala Ile Val
65                  70                  75                  80
Gln Thr Leu Val His Leu Met Asn Pro Glu Tyr Val Pro Lys Pro Cys
                85                  90                  95
Cys Ala Pro Thr Lys Leu Asn Ala Ile Ser Val Leu Tyr Phe Asp Asp
            100                 105                 110
Asn Ser Asn Val Ile Leu Lys Lys Tyr Arg Asn Met Val Val Arg Ala
        115                 120                 125
Cys Gly Cys His
    130

<210> SEQ ID NO 43
<211> LENGTH: 19
<212> TYPE: PRT
<213> ORGANISM: Artificial Sequence
<220> FEATURE:
<223> OTHER INFORMATION: Complement factor 5a receptor targeting
      inhibitor LRT20707
```

```
<220> FEATURE:
<221> NAME/KEY: MISC_FEATURE
<222> LOCATION: (1)..(19)
<223> OTHER INFORMATION: This sequence is part of a branched peptide.
<220> FEATURE:
<221> NAME/KEY: MISC_FEATURE
<222> LOCATION: (19)..(19)
<223> OTHER INFORMATION: Site of linkage in dendromer

<400> SEQUENCE: 43

Leu Arg Thr Trp Ser Arg Arg Ala Thr Arg Ser Thr Lys Thr Leu Lys
1               5                   10                  15

Val Val Lys

<210> SEQ ID NO 44
<211> LENGTH: 18
<212> TYPE: PRT
<213> ORGANISM: Artificial Sequence
<220> FEATURE:
<223> OTHER INFORMATION: Complement factor 5a receptor targeting
      inhibitor LRT20707
<220> FEATURE:
<221> NAME/KEY: MISC_FEATURE
<222> LOCATION: (1)..(18)
<223> OTHER INFORMATION: This sequence is part of a branched peptide.

<400> SEQUENCE: 44

Leu Arg Thr Trp Ser Arg Arg Ala Thr Arg Ser Thr Lys Thr Leu Lys
1               5                   10                  15

Val Val

<210> SEQ ID NO 45
<211> LENGTH: 20
<212> TYPE: PRT
<213> ORGANISM: Artificial Sequence
<220> FEATURE:
<223> OTHER INFORMATION: Complement factor 5a receptor targeting
      inhibitor LRT20707
<220> FEATURE:
<221> NAME/KEY: MISC_FEATURE
<222> LOCATION: (1)..(20)
<223> OTHER INFORMATION: This sequence is part of a branched peptide.
<220> FEATURE:
<221> NAME/KEY: SITE
<222> LOCATION: (19)..(20)
<223> OTHER INFORMATION: Sites of linkage in dendromer

<400> SEQUENCE: 45

Leu Arg Thr Trp Ser Arg Arg Ala Thr Arg Ser Thr Lys Thr Leu Lys
1               5                   10                  15

Val Val Lys Lys
            20

<210> SEQ ID NO 46
<211> LENGTH: 14
<212> TYPE: PRT
<213> ORGANISM: Artificial Sequence
<220> FEATURE:
<223> OTHER INFORMATION: Endothelin A receptor targeting inhibitor
      QGI10797
<220> FEATURE:
<221> NAME/KEY: MISC_FEATURE
<222> LOCATION: (1)..(14)
<223> OTHER INFORMATION: This sequence is part of a branched peptide.
<220> FEATURE:
<221> NAME/KEY: SITE
<222> LOCATION: (13)..(14)
<223> OTHER INFORMATION: Sites of linkage in dendromer
```

<400> SEQUENCE: 46

Gln Gly Ile Gly Ile Pro Leu Ile Thr Ala Glu Ile Lys Lys
1               5                   10

<210> SEQ ID NO 47
<211> LENGTH: 13
<212> TYPE: PRT
<213> ORGANISM: Artificial Sequence
<220> FEATURE:
<223> OTHER INFORMATION: Endothelin A receptor targeting inhibitor
      QGI10797
<220> FEATURE:
<221> NAME/KEY: MISC_FEATURE
<222> LOCATION: (1)..(13)
<223> OTHER INFORMATION: This sequence is part of a branched peptide.
<220> FEATURE:
<221> NAME/KEY: SITE
<222> LOCATION: (13)..(13)
<223> OTHER INFORMATION: Site of linkage in dendromer

<400> SEQUENCE: 47

Gln Gly Ile Gly Ile Pro Leu Ile Thr Ala Glu Ile Lys
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Endothelin A receptor targeting inhibitor
      QGI10797
<220> FEATURE:
<221> NAME/KEY: MISC_FEATURE
<222> LOCATION: (1)..(12)
<223> OTHER INFORMATION: This sequence is part of a branched peptide.

<400> SEQUENCE: 48

Gln Gly Ile Gly Ile Pro Leu Ile Thr Ala Glu Ile
1               5                   10

<210> SEQ ID NO 49
<211> LENGTH: 417
<212> TYPE: PRT
<213> ORGANISM: Homo sapiens
<220> FEATURE:
<221> NAME/KEY: MISC_FEATURE
<222> LOCATION: (1)..(417)
<223> OTHER INFORMATION: CPB1 human carboxypeptidase B-wild type

<400> SEQUENCE: 49

Met Leu Ala Leu Leu Val Leu Val Thr Val Ala Leu Ala Ser Ala His
1               5                   10                  15

His Gly Gly Glu His Phe Glu Gly Glu Lys Val Phe Arg Val Asn Val
                20                  25                  30

Glu Asp Glu Asn His Ile Asn Ile Ile Arg Glu Leu Ala Ser Thr Thr
            35                  40                  45

Gln Ile Asp Phe Trp Lys Pro Asp Ser Val Thr Gln Ile Lys Pro His
        50                  55                  60

Ser Thr Val Asp Phe Arg Val Lys Ala Glu Asp Thr Val Thr Val Glu
65                  70                  75                  80

Asn Val Leu Lys Gln Asn Glu Leu Gln Tyr Lys Val Leu Ile Ser Asn
                85                  90                  95

Leu Arg Asn Val Val Glu Ala Gln Phe Asp Ser Arg Val Arg Ala Thr
            100                 105                 110

```
Gly His Ser Tyr Glu Lys Tyr Asn Lys Trp Glu Thr Ile Glu Ala Trp
        115                 120                 125

Thr Gln Gln Val Ala Thr Glu Asn Pro Ala Leu Ile Ser Arg Ser Val
    130                 135                 140

Ile Gly Thr Thr Phe Glu Gly Arg Ala Ile Tyr Leu Leu Lys Val Gly
145                 150                 155                 160

Lys Ala Gly Gln Asn Lys Pro Ala Ile Phe Met Asp Cys Gly Phe His
                165                 170                 175

Ala Arg Glu Trp Ile Ser Pro Ala Phe Cys Gln Trp Phe Val Arg Glu
            180                 185                 190

Ala Val Arg Thr Tyr Gly Arg Glu Ile Gln Val Thr Glu Leu Leu Asp
        195                 200                 205

Lys Leu Asp Phe Tyr Val Leu Pro Val Leu Asn Ile Asp Gly Tyr Ile
    210                 215                 220

Tyr Thr Trp Thr Lys Ser Arg Phe Trp Arg Lys Thr Arg Ser Thr His
225                 230                 235                 240

Thr Gly Ser Ser Cys Ile Gly Thr Asp Pro Asn Arg Asn Phe Asp Ala
                245                 250                 255

Gly Trp Cys Glu Ile Gly Ala Ser Arg Asn Pro Cys Asp Glu Thr Tyr
            260                 265                 270

Cys Gly Pro Ala Ala Glu Ser Glu Lys Glu Thr Lys Ala Leu Ala Asp
        275                 280                 285

Phe Ile Arg Asn Lys Leu Ser Ser Ile Lys Ala Tyr Leu Thr Ile His
    290                 295                 300

Ser Tyr Ser Gln Met Met Ile Tyr Pro Tyr Ser Tyr Ala Tyr Lys Leu
305                 310                 315                 320

Gly Glu Asn Asn Ala Glu Leu Asn Ala Leu Ala Lys Ala Thr Val Lys
                325                 330                 335

Glu Leu Ala Ser Leu His Gly Thr Lys Tyr Thr Tyr Gly Pro Gly Ala
            340                 345                 350

Thr Thr Ile Tyr Pro Ala Ala Gly Gly Ser Asp Asp Trp Ala Tyr Asp
        355                 360                 365

Gln Gly Ile Arg Tyr Ser Phe Thr Phe Glu Leu Arg Asp Thr Gly Arg
    370                 375                 380

Tyr Gly Phe Leu Leu Pro Glu Ser Gln Ile Arg Ala Thr Cys Glu Glu
385                 390                 395                 400

Thr Phe Leu Ala Ile Lys Tyr Val Ala Ser Tyr Val Leu Glu His Leu
                405                 410                 415

Tyr
```

<210> SEQ ID NO 50
<211> LENGTH: 15
<212> TYPE: PRT
<213> ORGANISM: Artificial Sequence
<220> FEATURE:
<223> OTHER INFORMATION: WT leader sequence of CPB1 human carboxypeptidase B-wild type

<400> SEQUENCE: 50

```
Met Leu Ala Leu Leu Val Leu Val Thr Val Ala Leu Ala Ser Ala
1               5                   10                  15
```

<210> SEQ ID NO 51
<211> LENGTH: 423
<212> TYPE: PRT
<213> ORGANISM: Homo sapiens
<220> FEATURE:
<221> NAME/KEY: MISC_FEATURE
<222> LOCATION: (1)..(423)
<223> OTHER INFORMATION: CPB2 human carboxypeptidase B2, TAFI wild type

<400> SEQUENCE: 51

```
Met Lys Leu Cys Ser Leu Ala Val Leu Val Pro Ile Val Leu Phe Cys
1               5                   10                  15

Glu Gln His Val Phe Ala Phe Gln Ser Gly Gln Val Leu Ala Ala Leu
            20                  25                  30

Pro Arg Thr Ser Arg Gln Val Gln Val Leu Gln Asn Leu Thr Thr Thr
        35                  40                  45

Tyr Glu Ile Val Leu Trp Gln Pro Val Thr Ala Asp Leu Ile Val Lys
50                  55                  60

Lys Gln Val His Phe Phe Val Asn Ala Ser Asp Val Asp Asn Val
65                  70                  75                  80

Lys Ala His Leu Asn Val Ser Gly Ile Pro Cys Ser Val Leu Leu Ala
            85                  90                  95

Asp Val Glu Asp Leu Ile Gln Gln Ile Ser Asn Asp Thr Val Ser
            100                 105                 110

Pro Arg Ala Ser Ala Ser Tyr Tyr Glu Gln Tyr His Ser Leu Asn Glu
        115                 120                 125

Ile Tyr Ser Trp Ile Glu Phe Ile Thr Glu Arg His Pro Asp Met Leu
130                 135                 140

Thr Lys Ile His Ile Gly Ser Ser Phe Glu Lys Tyr Pro Leu Tyr Val
145                 150                 155                 160

Leu Lys Val Ser Gly Lys Glu Gln Thr Ala Lys Asn Ala Ile Trp Ile
            165                 170                 175

Asp Cys Gly Ile His Ala Arg Glu Trp Ile Ser Pro Ala Phe Cys Leu
        180                 185                 190

Trp Phe Ile Gly His Ile Thr Gln Phe Tyr Gly Ile Ile Gly Gln Tyr
    195                 200                 205

Thr Asn Leu Leu Arg Leu Val Asp Phe Tyr Val Met Pro Val Val Asn
210                 215                 220

Val Asp Gly Tyr Asp Tyr Ser Trp Lys Lys Asn Arg Met Trp Arg Lys
225                 230                 235                 240

Asn Arg Ser Phe Tyr Ala Asn Asn His Cys Ile Gly Thr Asp Leu Asn
            245                 250                 255

Arg Asn Phe Ala Ser Lys His Trp Cys Glu Glu Gly Ala Ser Ser Ser
        260                 265                 270

Ser Cys Ser Glu Thr Tyr Cys Gly Leu Tyr Pro Glu Ser Glu Pro Glu
    275                 280                 285

Val Lys Ala Val Ala Ser Phe Leu Arg Arg Asn Ile Asn Gln Ile Lys
290                 295                 300

Ala Tyr Ile Ser Met His Ser Tyr Ser Gln His Ile Val Phe Pro Tyr
305                 310                 315                 320

Ser Tyr Thr Arg Ser Lys Ser Lys Asp His Glu Glu Leu Ser Leu Val
            325                 330                 335

Ala Ser Glu Ala Val Arg Ala Ile Glu Lys Thr Ser Lys Asn Thr Arg
        340                 345                 350

Tyr Thr His Gly His Gly Ser Glu Thr Leu Tyr Leu Ala Pro Gly Gly
    355                 360                 365

Gly Asp Asp Trp Ile Tyr Asp Leu Gly Ile Lys Tyr Ser Phe Thr Ile
370                 375                 380
```

```
Glu Leu Arg Asp Thr Gly Thr Tyr Gly Phe Leu Leu Pro Glu Arg Tyr
385                 390                 395                 400

Ile Lys Pro Thr Cys Arg Glu Ala Phe Ala Ala Val Ser Lys Ile Ala
            405                 410                 415

Trp His Val Ile Arg Asn Val
            420

<210> SEQ ID NO 52
<211> LENGTH: 14
<212> TYPE: PRT
<213> ORGANISM: Artificial Sequence
<220> FEATURE:
<223> OTHER INFORMATION: PL3-AHB peptide derived from C5a anaphylatoxin

<400> SEQUENCE: 52

Gln Lys Lys Ile Glu Glu Ile Ala Ala Lys Tyr Lys His Ser
1               5                   10

<210> SEQ ID NO 53
<211> LENGTH: 13
<212> TYPE: PRT
<213> ORGANISM: Artificial Sequence
<220> FEATURE:
<223> OTHER INFORMATION: PL12-AHB peptide derived from C5a anaphylatoxin

<400> SEQUENCE: 53

Lys Tyr Lys His Ser Val Val Lys Lys Ser Asp Gly Ala
1               5                   10

<210> SEQ ID NO 54
<211> LENGTH: 17
<212> TYPE: PRT
<213> ORGANISM: Artificial Sequence
<220> FEATURE:
<223> OTHER INFORMATION: PL37-AHB peptide derived from C5a anaphylatoxin

<400> SEQUENCE: 54

Arg Ala Ala Arg Ile Ser Leu Gly Pro Arg Ser Ile Lys Ala Phe Thr
1               5                   10                  15

Glu

<210> SEQ ID NO 55
<211> LENGTH: 14
<212> TYPE: PRT
<213> ORGANISM: Artificial Sequence
<220> FEATURE:
<223> OTHER INFORMATION: PL61-AHB peptide derived from C5a anaphylatoxin

<400> SEQUENCE: 55

Leu Arg Ala Asn Ile Ser His Lys Asp Met Gln Leu Gly Arg
1               5                   10

<210> SEQ ID NO 56
<211> LENGTH: 510
<212> TYPE: PRT
<213> ORGANISM: Homo sapiens
<220> FEATURE:
<221> NAME/KEY: MISC_FEATURE
<222> LOCATION: (1)..(510)
<223> OTHER INFORMATION: Wild type BMP-6 protein sequence (BMP6_HUMAN)
```

<400> SEQUENCE: 56

```
Met Ala Pro Phe Glu Pro Leu Ala Ser Gly Ile Leu Leu Leu Leu Trp
1               5                   10                  15

Leu Ile Cys Gly Pro Pro Leu Arg Pro Leu Pro Ala Ala
            20                  25                  30

Ala Ala Ala Ala Gly Gly Gln Leu Gly Asp Gly Ser Pro Gly
            35              40                  45

Arg Thr Glu Gln Pro Pro Ser Pro Gln Ser Ser Ser Gly Phe Leu
        50                  55                  60

Tyr Arg Arg Leu Lys Thr Gln Glu Lys Arg Glu Met Gln Lys Glu Ile
65                  70                  75                  80

Leu Ser Val Leu Gly Leu Pro His Arg Pro Arg Pro Leu His Gly Leu
                85                  90                  95

Gln Gln Pro Gln Pro Pro Ala Leu Arg Gln Gln Glu Glu Gln Gln Gln
            100                 105                 110

Gln Gln Gln Leu Pro Arg Gly Glu Pro Pro Pro Gly Arg Leu Lys Ser
            115                 120                 125

Ala Pro Leu Phe Met Leu Asp Leu Tyr Asn Ala Leu Ser Ala Asp Asn
130                 135                 140

Asp Glu Asp Gly Ala Ser Glu Gly Glu Arg Gln Gln Ser Trp Pro His
145                 150                 155                 160

Glu Ala Ala Ser Ser Ser Gln Arg Arg Gln Pro Pro Pro Gly Ala Ala
                165                 170                 175

His Pro Leu Asn Arg Lys Ser Leu Leu Ala Pro Gly Ser Gly Ser Gly
            180                 185                 190

Gly Ala Ser Pro Leu Thr Ser Ala Gln Asp Ser Ala Phe Leu Asn Asp
            195                 200                 205

Ala Asp Met Val Met Ser Phe Val Asn Leu Val Glu Tyr Asp Lys Glu
210                 215                 220

Phe Ser Pro Arg Gln Arg His His Lys Glu Phe Lys Phe Asn Leu Ser
225                 230                 235                 240

Gln Ile Pro Glu Gly Glu Val Val Thr Ala Ala Glu Phe Arg Ile Tyr
                245                 250                 255

Lys Asp Cys Val Met Gly Ser Phe Lys Asn Gln Thr Phe Leu Ile Ser
            260                 265                 270

Ile Tyr Gln Val Leu Gln Glu His Gln His Arg Asp Ser Asp Leu Phe
            275                 280                 285

Leu Leu Asp Thr Arg Val Val Trp Ala Ser Glu Glu Gly Trp Leu Glu
290                 295                 300

Phe Asp Ile Thr Ala Thr Ser Asn Leu Trp Val Val Thr Pro Gln His
305                 310                 315                 320

Asn Met Gly Leu Gln Leu Ser Val Val Thr Arg Asp Gly Val His Val
                325                 330                 335

His Pro Arg Ala Ala Gly Leu Val Gly Arg Asp Gly Pro Tyr Asp Lys
            340                 345                 350

Gln Pro Phe Met Val Ala Phe Phe Lys Val Ser Glu Val His Val Arg
            355                 360                 365

Thr Thr Arg Ser Ala Ser Ser Arg Arg Arg Gln Gln Ser Arg Asn Arg
370                 375                 380

Ser Thr Gln Ser Gln Asp Val Ala Arg Val Ser Ser Ala Ser Asp Tyr
385                 390                 395                 400

Asn Ser Ser Glu Leu Lys Thr Ala Cys Arg Lys His Glu Leu Tyr Val
                405                 410                 415
```

```
Ser Phe Gln Asp Leu Gly Trp Gln Asp Trp Ile Ile Ala Pro Lys Gly
                420                 425                 430

Tyr Ala Ala Asn Tyr Cys Asp Gly Glu Cys Ser Phe Pro Leu Asn Ala
            435                 440                 445

His Met Asn Ala Thr Asn His Ala Ile Val Gln Thr Leu Val His Leu
        450                 455                 460

Met Asn Pro Glu Tyr Val Pro Lys Pro Cys Cys Ala Pro Thr Lys Leu
465                 470                 475                 480

Asn Ala Ile Ser Val Leu Tyr Phe Asp Asp Asn Ser Asn Val Ile Leu
                485                 490                 495

Lys Lys Tyr Arg Asn Met Val Val Arg Ala Cys Gly Cys His
            500                 505                 510

<210> SEQ ID NO 57
<211> LENGTH: 18
<212> TYPE: PRT
<213> ORGANISM: Artificial Sequence
<220> FEATURE:
<223> OTHER INFORMATION: Old leader peptide of BMP6_HUMAN

<400> SEQUENCE: 57

Met Ala Pro Phe Glu Pro Leu Ala Ser Gly Ile Leu Leu Leu Leu Trp
1               5                   10                  15

Leu Ile

<210> SEQ ID NO 58
<211> LENGTH: 21
<212> TYPE: PRT
<213> ORGANISM: Artificial Sequence
<220> FEATURE:
<223> OTHER INFORMATION: New leader peptide

<400> SEQUENCE: 58

Met Pro Gly Leu Gly Arg Arg Ala Gln Trp Leu Cys Trp Trp Trp Gly
1               5                   10                  15

Leu Leu Cys Ser Cys
            20

<210> SEQ ID NO 59
<211> LENGTH: 360
<212> TYPE: PRT
<213> ORGANISM: Artificial Sequence
<220> FEATURE:
<223> OTHER INFORMATION: Propeptide

<400> SEQUENCE: 59

Cys Gly Pro Pro Pro Leu Arg Pro Pro Leu Pro Ala Ala Ala Ala Ala
1               5                   10                  15

Ala Ala Gly Gly Gln Leu Leu Gly Asp Gly Gly Ser Pro Gly Arg Thr
            20                  25                  30

Glu Gln Pro Pro Pro Ser Pro Gln Ser Ser Ser Gly Phe Leu Tyr Arg
        35                  40                  45

Arg Leu Lys Thr Gln Glu Lys Arg Glu Met Gln Lys Glu Ile Leu Ser
    50                  55                  60

Val Leu Gly Leu Pro His Arg Pro Arg Pro Leu His Gly Leu Gln Gln
65                  70                  75                  80

Pro Gln Pro Pro Ala Leu Arg Gln Gln Glu Glu Gln Gln Gln Gln Gln
                85                  90                  95

Gln Leu Pro Arg Gly Glu Pro Pro Pro Gly Arg Leu Lys Ser Ala Pro
            100                 105                 110
```

Leu Phe Met Leu Asp Leu Tyr Asn Ala Leu Ser Ala Asp Asn Asp Glu
            115                 120                 125

Asp Gly Ala Ser Glu Gly Glu Arg Gln Gln Ser Trp Pro His Glu Ala
    130                 135                 140

Ala Ser Ser Ser Gln Arg Arg Gln Pro Pro Gly Ala Ala His Pro
145                 150                 155                 160

Leu Asn Arg Lys Ser Leu Leu Ala Pro Gly Ser Gly Ser Gly Gly Ala
                165                 170                 175

Ser Pro Leu Thr Ser Ala Gln Asp Ser Ala Phe Leu Asn Asp Ala Asp
            180                 185                 190

Met Val Met Ser Phe Val Asn Leu Val Glu Tyr Asp Lys Glu Phe Ser
    195                 200                 205

Pro Arg Gln Arg His His Lys Glu Phe Lys Phe Asn Leu Ser Gln Ile
210                 215                 220

Pro Glu Gly Glu Val Val Thr Ala Ala Glu Phe Arg Ile Tyr Lys Asp
225                 230                 235                 240

Cys Val Met Gly Ser Phe Lys Asn Gln Thr Phe Leu Ile Ser Ile Tyr
                245                 250                 255

Gln Val Leu Gln Glu His Gln His Arg Asp Ser Asp Leu Phe Leu Leu
            260                 265                 270

Asp Thr Arg Val Val Trp Ala Ser Glu Glu Gly Trp Leu Glu Phe Asp
    275                 280                 285

Ile Thr Ala Thr Ser Asn Leu Trp Val Val Thr Pro Gln His Asn Met
            290                 295                 300

Gly Leu Gln Leu Ser Val Val Thr Arg Asp Gly Val His Val His Pro
305                 310                 315                 320

Arg Ala Ala Gly Leu Val Gly Arg Asp Gly Pro Tyr Asp Lys Gln Pro
                325                 330                 335

Phe Met Val Ala Phe Phe Lys Val Ser Glu Val His Val Arg Thr Thr
            340                 345                 350

Arg Ser Ala Ser Ser Arg Arg Arg
    355                 360

<210> SEQ ID NO 60
<211> LENGTH: 132
<212> TYPE: PRT
<213> ORGANISM: Artificial Sequence
<220> FEATURE:
<223> OTHER INFORMATION: active domain

<400> SEQUENCE: 60

Gln Gln Ser Arg Asn Arg Ser Thr Gln Ser Gln Asp Val Ala Arg Val
1               5                   10                  15

Ser Ser Ala Ser Asp Tyr Asn Ser Ser Glu Leu Lys Thr Ala Cys Arg
                20                  25                  30

Lys His Glu Leu Tyr Val Ser Phe Gln Asp Leu Gly Trp Gln Asp Trp
            35                  40                  45

Ile Ile Ala Pro Lys Gly Tyr Ala Ala Asn Tyr Cys Asp Gly Glu Cys
    50                  55                  60

Ser Phe Pro Leu Asn Ala His Met Asn Ala Thr Asn His Ala Ile Val
65                  70                  75                  80

Gln Thr Leu Val His Leu Met Asn Pro Glu Tyr Val Pro Lys Pro Cys
                85                  90                  95

Cys Ala Pro Thr Lys Leu Asn Ala Ile Ser Val Leu Tyr Phe Asp Asp
            100                 105                 110

```
Asn Ser Asn Val Ile Leu Lys Lys Tyr Arg Asn Met Val Val Arg Ala
            115                 120                 125

Cys Gly Cys His
        130
```

<210> SEQ ID NO 61
<211> LENGTH: 4
<212> TYPE: PRT
<213> ORGANISM: Artificial Sequence
<220> FEATURE:
<223> OTHER INFORMATION: Cleavage site

<400> SEQUENCE: 61

```
Arg Arg Gln Gln
1
```

<210> SEQ ID NO 62
<211> LENGTH: 4
<212> TYPE: PRT
<213> ORGANISM: Artificial Sequence
<220> FEATURE:
<223> OTHER INFORMATION: Cleavage site mutation

<400> SEQUENCE: 62

```
Arg Arg Gln Ala
1
```

<210> SEQ ID NO 63
<211> LENGTH: 513
<212> TYPE: PRT
<213> ORGANISM: Homo sapiens
<220> FEATURE:
<221> NAME/KEY: MISC_FEATURE
<222> LOCATION: (1)..(513)
<223> OTHER INFORMATION: Wild type human BMP 6

<400> SEQUENCE: 63

```
Met Pro Gly Leu Gly Arg Arg Ala Gln Trp Leu Cys Trp Trp Trp Gly
1               5                   10                  15

Leu Leu Cys Ser Cys Cys Gly Pro Pro Pro Leu Arg Pro Pro Leu Pro
            20                  25                  30

Ala Ala Ala Ala Ala Ala Ala Gly Gly Gln Leu Leu Gly Asp Gly Gly
        35                  40                  45

Ser Pro Gly Arg Thr Glu Gln Pro Pro Ser Pro Gln Ser Ser Ser
    50                  55                  60

Gly Phe Leu Tyr Arg Arg Leu Lys Thr Gln Glu Lys Arg Glu Met Gln
65                  70                  75                  80

Lys Glu Ile Leu Ser Val Leu Gly Leu Pro His Arg Pro Arg Pro Leu
                85                  90                  95

His Gly Leu Gln Gln Pro Gln Pro Pro Ala Leu Arg Gln Gln Glu Glu
            100                 105                 110

Gln Gln Gln Gln Gln Gln Leu Pro Arg Gly Glu Pro Pro Pro Gly Arg
        115                 120                 125

Leu Lys Ser Ala Pro Leu Phe Met Leu Asp Leu Tyr Asn Ala Leu Ser
    130                 135                 140

Ala Asp Asn Asp Glu Asp Gly Ala Ser Glu Gly Glu Arg Gln Gln Ser
145                 150                 155                 160

Trp Pro His Glu Ala Ala Ser Ser Ser Gln Arg Arg Gln Pro Pro Pro
                165                 170                 175

Gly Ala Ala His Pro Leu Asn Arg Lys Ser Leu Leu Ala Pro Gly Ser
            180                 185                 190
```

```
Gly Ser Gly Gly Ala Ser Pro Leu Thr Ser Ala Gln Asp Ser Ala Phe
            195                 200                 205

Leu Asn Asp Ala Asp Met Val Met Ser Phe Val Asn Leu Val Glu Tyr
210                 215                 220

Asp Lys Glu Phe Ser Pro Arg Gln Arg His His Lys Glu Phe Lys Phe
225                 230                 235                 240

Asn Leu Ser Gln Ile Pro Glu Gly Glu Val Val Thr Ala Ala Glu Phe
                245                 250                 255

Arg Ile Tyr Lys Asp Cys Val Met Gly Ser Phe Lys Asn Gln Thr Phe
            260                 265                 270

Leu Ile Ser Ile Tyr Gln Val Leu Gln Glu His Gln His Arg Asp Ser
        275                 280                 285

Asp Leu Phe Leu Leu Asp Thr Arg Val Val Trp Ala Ser Glu Glu Gly
290                 295                 300

Trp Leu Glu Phe Asp Ile Thr Ala Thr Ser Asn Leu Trp Val Val Thr
305                 310                 315                 320

Pro Gln His Asn Met Gly Leu Gln Leu Ser Val Val Thr Arg Asp Gly
                325                 330                 335

Val His Val His Pro Arg Ala Ala Gly Leu Val Gly Arg Asp Gly Pro
            340                 345                 350

Tyr Asp Lys Gln Pro Phe Met Val Ala Phe Phe Lys Val Ser Glu Val
        355                 360                 365

His Val Arg Thr Thr Arg Ser Ala Ser Ser Arg Arg Arg Gln Gln Ser
    370                 375                 380

Arg Asn Arg Ser Thr Gln Ser Gln Asp Val Ala Arg Val Ser Ser Ala
385                 390                 395                 400

Ser Asp Tyr Asn Ser Ser Glu Leu Lys Thr Ala Cys Arg Lys His Glu
                405                 410                 415

Leu Tyr Val Ser Phe Gln Asp Leu Gly Trp Gln Asp Trp Ile Ile Ala
            420                 425                 430

Pro Lys Gly Tyr Ala Ala Asn Tyr Cys Asp Gly Glu Cys Ser Phe Pro
        435                 440                 445

Leu Asn Ala His Met Asn Ala Thr Asn His Ala Ile Val Gln Thr Leu
450                 455                 460

Val His Leu Met Asn Pro Glu Tyr Val Pro Lys Pro Cys Cys Ala Pro
465                 470                 475                 480

Thr Lys Leu Asn Ala Ile Ser Val Leu Tyr Phe Asp Asp Asn Ser Asn
                485                 490                 495

Val Ile Leu Lys Lys Tyr Arg Asn Met Val Val Arg Ala Cys Gly Cys
            500                 505                 510

His

<210> SEQ ID NO 64
<211> LENGTH: 431
<212> TYPE: PRT
<213> ORGANISM: Homo sapiens
<220> FEATURE:
<221> NAME/KEY: MISC_FEATURE
<222> LOCATION: (1)..(431)
<223> OTHER INFORMATION: Wild type human BMP 7

<400> SEQUENCE: 64

Met His Val Arg Ser Leu Arg Ala Ala Ala Pro His Ser Phe Val Ala
1               5                   10                  15

Leu Trp Ala Pro Leu Phe Leu Leu Arg Ser Ala Leu Ala Asp Phe Ser
            20                  25                  30
```

```
Leu Asp Asn Glu Val His Ser Ser Phe Ile His Arg Leu Arg Ser
     35                  40                  45

Gln Glu Arg Arg Glu Met Gln Arg Glu Ile Leu Ser Ile Leu Gly Leu
 50                  55                  60

Pro His Arg Pro Arg Pro His Leu Gln Gly Lys His Asn Ser Ala Pro
 65                  70                  75                  80

Met Phe Met Leu Asp Leu Tyr Asn Ala Met Ala Val Glu Glu Gly Gly
                 85                  90                  95

Gly Pro Gly Gly Gln Gly Phe Ser Tyr Pro Tyr Lys Ala Val Phe Ser
                100                 105                 110

Thr Gln Gly Pro Pro Leu Ala Ser Leu Gln Asp Ser His Phe Leu Thr
             115                 120                 125

Asp Ala Asp Met Val Met Ser Phe Val Asn Leu Val Glu His Asp Lys
130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
                180                 185                 190

Ser Val Tyr Gln Val Leu Gln Glu His Leu Gly Arg Glu Ser Asp Leu
            195                 200                 205

Phe Leu Leu Asp Ser Arg Thr Leu Trp Ala Ser Glu Glu Gly Trp Leu
210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
                260                 265                 270

Lys Gln Pro Phe Met Val Ala Phe Phe Lys Ala Thr Glu Val His Phe
            275                 280                 285

Arg Ser Ile Arg Ser Thr Gly Ser Lys Gln Arg Ser Gln Asn Arg Ser
290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
                340                 345                 350

Gly Tyr Ala Ala Tyr Tyr Cys Glu Gly Glu Cys Ala Phe Pro Leu Asn
            355                 360                 365

Ser Tyr Met Asn Ala Thr Asn His Ala Ile Val Gln Thr Leu Val His
370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
                420                 425                 430

<210> SEQ ID NO 65
<211> LENGTH: 20
<212> TYPE: PRT
```

<213> ORGANISM: Artificial Sequence
<220> FEATURE:
<223> OTHER INFORMATION: Wild type leader peptide

<400> SEQUENCE: 65

Met Pro Gly Leu Gly Arg Arg Ala Gln Trp Leu Cys Trp Trp Trp Gly
1               5                   10                  15
Leu Leu Cys Ser
            20

<210> SEQ ID NO 66
<211> LENGTH: 21
<212> TYPE: PRT
<213> ORGANISM: Artificial Sequence
<220> FEATURE:
<223> OTHER INFORMATION: Optimized leader peptide

<400> SEQUENCE: 66

Met Arg Ala Pro Ala Gln Ile Phe Gly Phe Leu Leu Leu Leu Phe Pro
1               5                   10                  15
Gly Thr Cys Phe Ala
            20

<210> SEQ ID NO 67
<211> LENGTH: 63
<212> TYPE: PRT
<213> ORGANISM: Homo sapiens
<220> FEATURE:
<221> NAME/KEY: MISC_FEATURE
<222> LOCATION: (1)..(63)
<223> OTHER INFORMATION: IgG Hinge region

<400> SEQUENCE: 67

Arg Trp Pro Glu Ser Pro Lys Ala Gln Ala Ser Ser Val Pro Thr Ala
1               5                   10                  15
Gln Pro Gln Ala Glu Gly Ser Leu Ala Lys Ala Thr Ala Pro Ala Thr
                20                  25                  30
Thr Arg Asn Thr Gly Arg Gly Gly Glu Glu Lys Lys Lys Glu Lys Glu
            35                  40                  45
Lys Glu Glu Gln Glu Glu Arg Glu Thr Lys Thr Pro Glu Cys Pro
        50                  55                  60

<210> SEQ ID NO 68
<211> LENGTH: 93
<212> TYPE: PRT
<213> ORGANISM: Homo sapiens
<220> FEATURE:
<221> NAME/KEY: MISC_FEATURE
<222> LOCATION: (1)..(93)
<223> OTHER INFORMATION: CD59 PI anchor

<400> SEQUENCE: 68

Gln Cys Tyr Asn Cys Pro Asn Pro Thr Ala Asp Cys Lys Thr Ala Val
1               5                   10                  15
Asn Cys Ser Ser Asp Phe Asp Ala Cys Leu Ile Thr Lys Ala Glu Leu
                20                  25                  30
Gly Tyr His Tyr Val Ala Gln Ala Gly Arg Arg Gln Ser Ser His Phe
            35                  40                  45
Ser Leu Leu Lys Cys Trp Asp Tyr Arg Cys Glu Pro Ser His Trp Pro
        50                  55                  60

```
His Cys Pro Tyr Phe Asn Trp Gly Tyr Lys Cys Ile Thr Ser Val Gly
 65                  70                  75                  80

Ser Leu Ser Ile Ala Ile Ser Thr Thr Ser Gln Pro Ala
                 85                  90

<210> SEQ ID NO 69
<211> LENGTH: 4
<212> TYPE: PRT
<213> ORGANISM: Artificial Sequence
<220> FEATURE:
<223> OTHER INFORMATION: Core of octameric dendromer
<220> FEATURE:
<221> NAME/KEY: MISC_FEATURE
<222> LOCATION: (1)..(3)
<223> OTHER INFORMATION: Sites of linkage in dendromer
<220> FEATURE:
<221> NAME/KEY: MISC_FEATURE
<222> LOCATION: (1)..(4)
<223> OTHER INFORMATION: This sequence is part of a branched peptide.
<220> FEATURE:
<221> NAME/KEY: MISC_FEATURE
<222> LOCATION: (4)..(4)
<223> OTHER INFORMATION: Any amino acid

<400> SEQUENCE: 69

Lys Lys Lys Xaa
1
```

THERAPEUTIC COMPOSITION FOR USE IN THE TREATMENT OF COVID-19 AND OTHER CYTOKINE STORM ASSOCIATED DISORDERS

The present invention is directed to a therapeutic composition for use in the treatment of COVID-19 and other cytokine storm associated disorders.

REFERENCE TO A SEQUENCE LISTING

The instant application contains a sequence listing which has been submitted in ASCII format via EFS-Web and is hereby incorporated by reference in its entirety. Said ASCII copy, created on Jul. 9, 2020 is named Sequence_Listing_222552_602954.txt and is 66,802 bytes in size.

FIELD OF THE INVENTION

Pathogenic corona viruses (SARS, MRSA, SARS-nCov2) are single positive RNA strand viruses with a wide spectrum of hosts and a strong ability to mutate at high rate, spread rapidly by waste, contacts and aerosols, and only a very limited set of treatments are available to protect infected patients.

The "corona-like" virus structure itself consists of the positive strand RNA packaged into the core of the virus, said core comprising membrane proteins and the spike protein. Membrane proteins support the viral morphogenesis, and the spike protein is a glycoprotein that attaches the virion to the cell membrane by interacting with the host receptor, thereby initiating the infection of the cells.

PRIOR ART

Clearly, the spike proteins as well as the other viral proteins are under intense study and huge effort is made to develop new rational antiviral treatment as well as vaccines. Currently discussed, antiviral treatment and drug candidates are: Remdesivir (viral polymerase inhibitor), Umifenovir (Fusion inhibitor), Lopinavir (Retrovirus protease inhibitor), Ritonavir (Retrovirus protease inhibitor) and Hydroxychloroquine (anti malaria drug).

A common factor in all of the known antiviral drugs is that they are highly toxic. This is tolerable as long as the application is life saving or preventing a severely debilitating outcome of the diseases. In many cases, however, the viral disease symptoms that may trigger the treatment are mild and may remain mild, rendering the toxic antiviral drug too dangerous to apply, or the side effects in severe cases of the viral infection actually further hurt the patients that already suffer from lung, liver, and/or intestinal symptoms.

OBJECT

It is an object of the present invention to provide another therapeutic approach. Particularly the inventor analysed the known mechanism of the viral infection, the progress of the infection, and the response of the human body. Critical elements in the physiological response were identified in order to design new drug candidates that shall help the body to hinder the progress of the viral infection, stopping the debilitating side effects and consequences of the disease.

INVENTION

Disclosed herein is a therapeutic composition for use in the treatment of COVID-19 and other cytokine storm associated disorders, wherein the therapeutic composition comprises at least one active agent being selected from the following active agent groups a) to e):

a) complement factor 3-targeting inhibitors,
b) carboxypeptidase B enzymes,
c) complement factor 5a receptor-targeting inhibitors,
d) endothelin A receptor-targeting inhibitors,
e) bone morphogenetic proteins.

Further disclosed is a method of treating COVID-19 and other cytokine storm associated disorders, wherein said method comprises administering an effective amount of at least one active agent being selected from the abovementioned active agent groups a) to e).

As used herein, the term "therapeutic composition" refers to a composition to be administered as a therapeutic treatment to a subject suffering from a disorder.

As used herein, the term "treatment" in the context of the administration to a subject refers to the reduction or inhibition of the progression and/or duration of disorder.

As used herein, the term "subject" refers to a mammal, most preferably a human.

As used herein, the term "composition" refers to an effective amount of one or more active agents, optionally in combination with pharmaceutical acceptable carriers and/or excipients.

By "pharmaceutically acceptable," is meant a compound that is not biologically or otherwise undesirable, that is, the compound may be incorporated into a topical formulation of the invention and administered to a patient without causing any undesirable biological effects or interacting in a deleterious manner with any of the other components of the formulation in which it is contained.

As used herein, the term "active agent" refers to a compound being effective in the treatment of a disorder, when being administered in an effective amount to a subject suffering from a disorder.

As used herein, the term "effective amount" refers to the amount of a treatment that is sufficient to result in the prevention of the development, recurrence, or onset of a condition being associated with a cytokine storm, and one or more symptoms thereof, to enhance or improve the prophylactic effect(s) of another therapy, reduce the severity, the duration of a cytokine storm associated disorder, ameliorate one or more symptoms of a condition being associated with a cytokine storm, prevent the advancement or recurrence of a cytokine storm, cause regression of a disorder being associated with a cytokine storm.

As used herein, the term "cytokine storm associated disorder" refers to a disorder that may result in a condition called "cytokine storm". The cytokine storm is characterized by unusual high blood levels of cytokines, such as chemokines, interferons, interleukins, lymphokines as compared to the corresponding blood levels of said cytokines in a healthy subject. Particularly relevant are the blood levels of inflammatory cytokines interleukin-1 (IL-1), IL-6, IL-12, and IL-18, tumor necrosis factor alpha (TNF-α), interferon gamma (IFNγ), granulocyte-macrophage colony stimulating factor (GM-CSF) and Transforming Growth Factor (TGF).

If the blood level of at least one inflammatory cytokine is raised in a subject by more than 10%, more than 20% or even more than 30% as compared to the corresponding blood level(s) of said cytokine(s) in a healthy subject, this is an indicator for an onset or for the presence of a cytokine storm. If the blood level of two or more inflammatory cytokines is raised in a subject by more than 10%, more than 20% or even more than 30% as compared to the corresponding blood level(s) of said cytokine(s) in a healthy subject, this is an even more clear indicator for an onset or for the presence of a cytokine storm.

Cytokine storm may be induced by various instances, including but not limited to infection with SARS COV-2 virus, any other corona viruses and any hemorrhagic fever causing viruses. It may also be induced by other physiological states and disorders.

The term "cytokine storm associated disorder" includes any disorder of a subject, that may result in a "cytokine storm" to occur. Examples for cytokine storm associated disorders that may be treated in accordance with the present invention are COVID-19, Hemorrhagic fever diseases, Allergy, Alzheimer's disease in CNS, ARDS/respiratory distress, Bechet's disease, bronchial asthma, capillary leak syndrome, ischemia, ischemia-reperfusion, chronic lung disease, immunocomplex glomerulonephritis, Churg-Strauss syndrome, Cystic fibrosis, Mediterranean fever Guillain-Barre, Cardiac ischemia and infarct reperfusion, Kimura's disease, Multiple Sclerosis, MS Meningitis Pancreatitis, Preeclampsia, Retinitis, Allogenic graft rejection, chronic inflammation, septic shock, acute ischemia, trauma and surgery, cardiac pathology and multiple organ failure, allotransplantation, asthma, acute respiratory distress syndrome, arthus reaction, burns injuries, Crohn's disease, dermatomyositis, drug-induced pseudoallergy, Forssman shock, glomerulonephritis, hemolytic anemia, hemorrhagic shock, hemodialysis reactions, hereditary angeoderma, Huntington's disease, infertility as a result of spontaneous abortion, ischemia reperfusion injuries, human complex-induced vasculitis, multiple sclerosis, myasthenia gravis, Pick's disease, paroxysmal nocturnal hemoglobinuria, post-bypass syndrome, psoriasis, rheumatoid arthritis and septic shock.

BRIEF DESCRIPTION OF THE FIGURES

FIG. 4 shows the expression cassette designed for the recombinant bone morphogenetic protein.

FIG. 5 shows that an injection of 1 µg/kg PR226MAP peptide does not induce any cardiovascular change but abrogates the lethal effects of the subsequent challenge with a lethal dose of C5a.

FIG. 8A shows the effective inhibition of smooth muscle contraction in femoral artery by treatment with the inventive peptides capable of blocking ET-A receptors.

FIG. 8B shows the effective inhibition of smooth muscle contraction in carotid artery by treatment with the inventive peptides capable of blocking ET-A receptors.

DETAILED DESCRIPTION OF INVENTION

Figure 1:
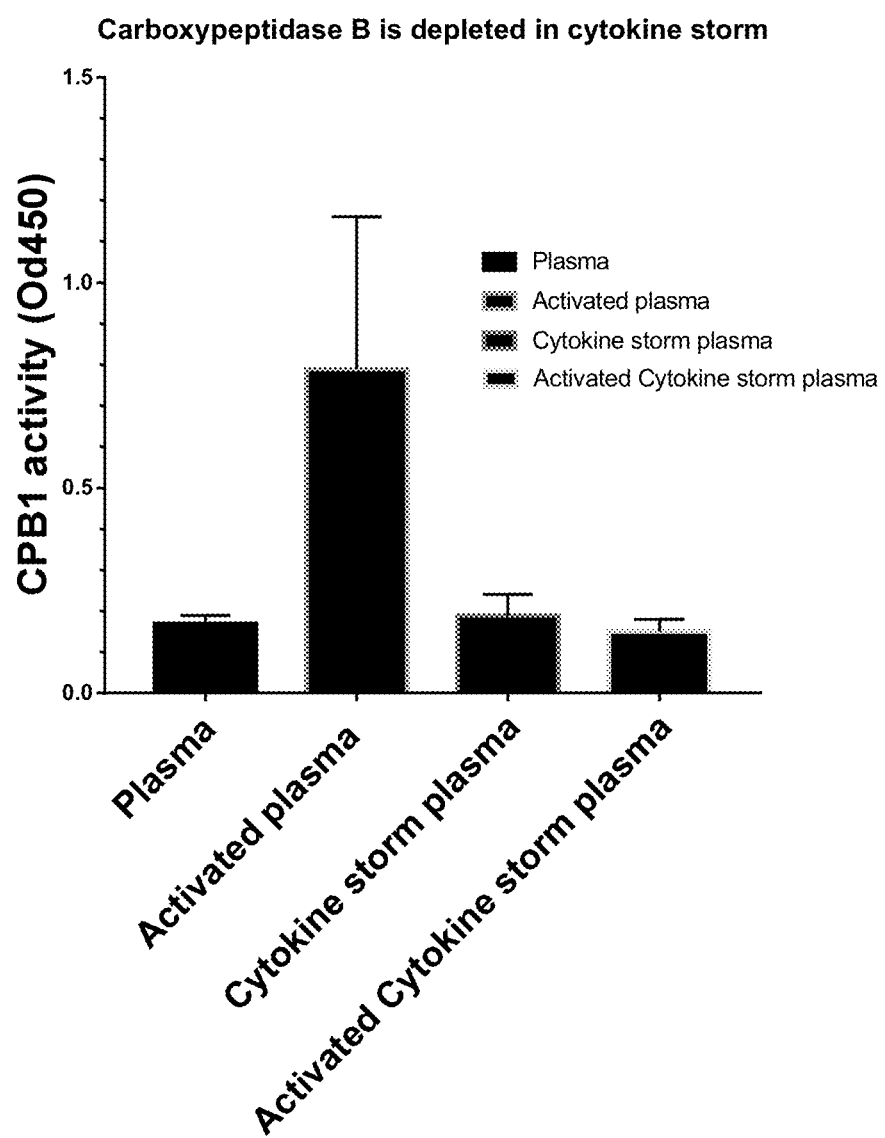
FIG. 1 shows the carboxypeptidase B enzyme activity in plasma, activated plasma, cytokine storm plasma and activated cytokine storm plasma.

The complement system is a part of the immune system. Over 30 proteins and protein fragments make up the complement system, including serum proteins, and cell membrane receptors. When stimulated by one of several triggers, proteases in the system cleave specific proteins to release cytokines and initiate an amplifying cascade of further cleavages. The end result of this complement activation or complement fixation cascade is stimulation of phagocytes to clear foreign and damaged material, inflammation to attract additional phagocytes, and activation of the cell-killing membrane attack complex.

Any process that activates the complement system goes through a series of positive feedback loops. Complement activation releases anaphylatoxins, C3a, C4a and C5a, all of which are powerful signaling molecules. The C5a gets mobilized, activated and released a substantial number of mediators. These factors in turn cause pulmonary hypertension, vascular dilation, together with the membrane attack complex cause vascular leakage, hypotension, hypoxia, acidosis, vasoconstriction, more hypoxia, intestinal symptoms and bacterial leakage, endotoxemia, fever, more complement activation, more granulocyte activation, more endothelial damage, and finally severe pulmonary hemorrhage, and cardiovascular damage. The major mediators of this process are the cytokines. Therefore, this process is also known as cytokine storm.

Once this cytokine storm is fully developed, it is irreversible, and most of the cases causes multiple organ failure, and death. Cytokine storm plays key role in cardiovascular-pulmonary collapse that is central element in death caused by hemorrhagic viruses, blood lost induced hemorrhagic shock, bacterial septic shock, pancreatitis, and most of systemic inflammatory shock diseases, drug-adverse reactions, CAR-T cell therapy adverse reactions. Further, it is known to be one of the reasons for many fatal cases of COVID-19.

The cytokine storm being a devastating medical disorder, it is disclosed a novel and effective treatment that reduces, diminishes and abolishes the devastating physiological effects of the cytokine storm. The goal of the treatment is avoiding immunosuppression while the cytokine storm is limited and remains at levels compatible with healing from the disease state that induced it.

Particularly, it is disclosed a treatment directed to a set of 5 targets participating in eliciting, amplifying and otherwise exacerbating the cytokine storm. These targets were rationally selected with expertise from hundreds of molecules participating in the onset and amplification of the cytokine storm.

It is disclosed a therapeutic composition for use in the treatment of COVID-19 and other cytokine storm associated disorders. By comprising at least one active agent selected from the following active agent groups:

a) complement factor 3-targeting inhibitors,
b) carboxypeptidase B enzymes,
c) complement factor 5a receptor-targeting inhibitors,
d) endothelin A receptor-targeting inhibitors,
e) bone morphogenetic proteins.

the therapeutic composition of the present invention provides means for effectively treating COVID-19 and other cytokine storm associated disorders. In some embodiments of the invention the therapeutic composition used comprises at least two, three, four or five distinct active agents being selected from at least two, three, four or five of the active agent groups a) to e).

a) Complement Factor 3-Targeting Inhibitor of Complement Activation Cascade

The root cause of the cytokine storm is the rapid and out of control complement system activation and while the triggering factors counts in dozens, and each of them result in a protease activity called C3 convertase (embodied in various forms) sharing common feature to be capable of specifically cleaving the C3 (complement factor 3) into C3a and C3b components, creating an active C3b, that itself acts as a C3 convertase via the C3b cleavage product. Targeting C3 and preventing the positive feedback loop is the first target selected.

Therefore, the present invention encompasses a therapeutic composition comprising at least one complement factor 3-targeting inhibitor of complement activation cascade. In some embodiments the complement factor 3-targeting inhibitor is a direct inhibitor of the complement factor 3 receptor. In other embodiments the complement factor 3-targeting inhibitor is an inhibitor of the complement factor 3 receptor activity through reducing the release of C3a anaphylatoxin. By reducing the release of C3a anaphylatoxins the activity of the complement factor 3 receptor can be reduced indirectly, that is, without using direct complement receptor 3 inhibitors.

C3 is the central element of the complement activation pathway, and blocking excess C3 activation blocks all the anaphylatoxin production, including subsequent raise of the cytokine storm. However, according to one aspect of the invention, C3 and its activity shall not be eliminated completely, as it is essential for the protection from microbes and for development of proper immune reaction. This is why in some embodiments the complement factor 3-targeting inhibitor is an inhibitor of the complement factor 3 receptor activity through reducing the release of C3a anaphylatoxin. This allows better fine tuning of complement factor 3 receptor activity.

In order to provide a complement inhibitor that acts fast, reversibly and without accumulation of toxic byproduct, the inventor has analyzed the human C3 protein with a proprietary algorithm implemented in C language and designed a series of peptides that were tested for their ability for inhibiting complement activity in a hemolysis assay. The inventor found that out of a library of 19 peptides 7 peptides inhibited the complement of complement mediated hemolysis very strong (80% or higher inhibition), 4 peptides inhibited hemolysis strong (40% or higher inhibition), 5 peptides had moderate inhibitor activity (20% or higher inhibition) and 4 peptides had low inhibitor activity (less than 20% inhibition) under the test conditions.

Accordingly, in some embodiments of the inventive therapeutic composition the complement factor 3-targeting inhibitor of complement activation cascade of active agent group a) is selected from the following group of peptides:
AP1314, LTA1309, DDL1619, SDK1606, SDA984, SDK1709, VQA1857, QAL1363, NIF1464, LHL1431, QRS1008, KRP1057, ERL1041, LNC1538, LSR1099, ESA1331, GQW1513, IAV1501, LRL1384 and TAY1409
having the amino acid sequences as specified in SEQ IDs Nos. 1-20.

The one letter code amino acid sequences and the hemolysis inhibition properties of said peptides are indicated in Table 1 of the examples further below.

b) Carboxypeptidase B Enzyme

Whenever there is complement activation, the cleavage of key components C3, C4 and C5 results in massive release of respective anaphylatoxins. Each of them is a single chain, 74 amino acid long amino terminal fragment of the respective complement factor (complement factor 3, 4 and 5), and each of them is terminated with an arginine amino acid at their carboxyterminal end. While all of them are powerful mediators, their activity is strongly diminished by the loss of the carboxy terminal arginine.

C5a is an effective chemoattractant, initiating accumulation of phagocytic cells at sites of infection or recruitment of antigen-presenting cells to lymph nodes. C5a also modulates the balance between activating versus inhibitory IgG Fc receptors on leukocytes by increasing it, thereby enhancing the (auto)immune response and triggering a genuine cytokine storm.

The anaphylatoxins and many of the messengers amplifying cytokine storm are peptides with an amino acid arginine at the carboxy terminus. The enzyme that removes that arginine renders the specific messengers and anaphylatoxins lose or reduce or change their biological activity. However, the inventor has found that this enzyme activity is very low in plasma. What is more, it is rapidly depleted as infection, hemorrhage, hypoxia develops, blood coagulation triggered (see Examples further below), in each case when systemic complement activation occurs, resulting in allowing anaphylatoxins to act at their full potential to trigger the positive feedback that results in Cytokine storm.

For removing the terminal arginine of peptides there is a set of enzymes called carboxypeptidase (E.C. numbers: 3.4.16 through 3.4.18), a subgroup consists of basic carboxypeptidases that specialize in removing basic amino acids Arg and Lys from the carboxy terminus of the peptide. It turned out that there is one enzyme specialized for converting C5a into desArg C5a. What is more, it has been shown that it is rapidly lost by self-inactivation.

Replenishing this enzyme, is expected to protect the patient from the excess power of these mediators, coagulation system malfunctions and granulocyte leukocyte activation and chemoattraction to the shock organs. Therefore, the present invention encompasses a therapeutic composition comprising at least carboxypeptidase B enzyme.

In some embodiments of the inventive therapeutic composition, said composition comprises as an active agent carboxypeptidase B enzyme being selected from the carboxypeptidases EC 3.4.16-3.4.18.

Further, the inventor has developed recombinant carboxypeptidase B enzymes having the amino acid sequences as specified in SEQ IDs No. 21-22. Said enzymes may be used in the treatment of cytokine associated disorders such as COVID-19. Therefore, in some embodiments of the inventive therapeutic composition said composition comprises as an active agent one of the aforementioned recombinant carboxypeptidase B enzymes. The one letter code amino acid sequences of said enzymes are indicated in the examples further below.

Said recombinant carboxypeptidase B enzyme can be obtained by a method comprising the following steps:
firstly introducing plasmids with recombinant carboxypeptidase B protogene sequence into *Escherichia coli* cells to construct a recombinant engineering strain,
fermenting for inducing and expressing recombinant carboxypeptidase B protogene (proenzyme),
additional renaturation, pancreatin conversion as well as separation, and
purification to obtain carboxypeptidase B enzyme.

The present application also encompasses a nucleic acid encoding recombinant carboxypeptidase B enzyme. Further, it is disclosed a lentiviral vector comprising this nucleic acid. In addition, it is disclosed a plasmid comprising this nucleic acid and a cell line comprising said plasmid. Furthermore, it is disclosed a method of producing recombinant carboxypeptidase B enzyme by cultivating a cell comprising the plasmid.

c) Complement Factor 5a Receptor-Targeting Inhibitor of Complement Activation Cascade By using one or both of the aforementioned active agents of groups a) and b), it is possible to control complement activation through inhibiting complement factor 3 and adding Carboxypeptidase B enzyme to keep the desArg form of the newly generated anaphylatoxins and disturbance in the coagulation system. This could significantly reduce the chance of the viral infection to turn into full cytokine storm.

However, a prolonged release and accumulation of C5a, even a very minuscule amounts on the site of the virus infection or tissue damage would still be able to activate attract and granulocytes and cause massive degranulation in the affected tissue, causing irreversible tissue damage. The C5a acting on its receptor is the main culprit in this process. It has been found that this receptor is one of the most sensitive receptors in cell signaling. The inventor has noted that picomolar quantities of C5a can trigger the intracellular activation signal and increase of $Ca^{++}$ levels.

C5a is the most powerful of the anaphylatoxins, and it exerts massive effect on cell expressing its receptor. These cells are heavily involved in the cytokine storm and induce the production of a vast array of secondary messengers, regardless of C5a has or lacks the terminal arginine. The nature of the effect may change though, but if the receptor is blocked, the overactivation of the cells involved in triggering the cytokine storm may be blocked, and kept at acceptable level, not threatening the patient's life or tissue integrity.

Therefore, the present invention encompasses a therapeutic composition comprising at least one complement factor 5a receptor-targeting inhibitor of complement activation cascade involved in the cytokine storm induction. In some embodiments the complement factor 5a receptor-targeting inhibitor is an inhibitor of the complement factor 5a receptor. In some embodiments the complement factor 5a receptor-targeting inhibitor is a competitor of the complement factor 5a or a fragment thereof. In some embodiments the complement factor 5a targeting inhibitor is not a competitor for the binding sites for the complement factor 5a, but interacts in another way with the complement factor 5a receptor, thereby inhibiting complement activation cascade. The inventor has synthesized and tested a large number of peptide-based C5aR agonists and antagonists, both, in vitro and in vivo. However, in many cases the beneficial effects do not materialize to the required extent. Particularly, some of the inhibitory variants of the peptides are not sufficiently compete with naturally occurring level of C5a in vivo for the ligand binding.

In some embodiments of the present invention, the complement factor 5a receptor-targeting inhibitor of complement activation cascade of active agent group c) is selected from the group of peptides:

LRT2463, LRT10353, LRT20707, DYG2094 and HWP1667 having the amino acid sequences as specified in SEQ IDs No. 23-27.

The one letter code amino acid sequences of said peptides are indicated in Table 3 of the examples further below. Said peptides have been shown to be very effective inhibitors of complement factor 5a receptor, both, in vitro and in vivo.

These peptides are considered potentially useful in clinical applications, but the observed biphasic activity of the most promising one (PR226), that it acted as inhibitor at high concentration and activator as low concentration, was a property that questioned the safety of the peptide for human use. However, the inventor has designed an oligomeric form of the peptide, a dendrimer, that increased its activity 10,000-fold, and the receptor inhibitory activity increased from femtomolar to 200 nM levels, a tremendous potential.

The activity in vivo, in rat and pig models, is shown in the examples below. Further, it has been shown that the peptide can be delivered in vivo very safely, even at very high concentration. The reason is that the peptide immediately binds to the erythrocyte surfaces and forms a stable membrane bound pool that is completely inert to erythrocytes, but upon contact with C5aR bearing cells, the inhibitory effect is fully exhibited. In addition, in the membrane bound state, the peptide remains active for at least 12 hours. Therefore, it is a very effective C5aR inhibitor.

d) Endothelin a Receptor-Targeting Inhibitor of Extravasation

The inventor has observed that activated macrophages and leukocytes do not do any harm while in the circulation. They do not act until they are surrounded by live, healthy erythrocytes. Particularly, they need to undergo extravasation, moving out of the capillaries into the affected tissue parenchyma.

Further, the inventor has identified that endothelin receptor is one of the bottleneck elements in the very complex and highly redundant process of extravasation. Particularly, the inventor noted that the process of extravasation is controlled by the endothelial cells. They open the gates upon the signal delivered by the endothelin peptide and engaging the endothelin A receptor on their surface. If said gates are not opened, the activated leukocytes cannot pass through the tightly bound endothelial membrane.

Therefore, the inventor has picked this as the fourth target in the treatment of cytokine storm. Particularly, the inventor has postulated that blocking extravasation could be the solution to down regulate the overactivated cells and prevent them from causing irreversible tissue damage.

Therefore, the present invention encompasses a therapeutic composition comprising at least one endothelin A receptor-targeting inhibitor of cytokine storm activation cascade. In some embodiments the endothelin A receptor-targeting inhibitor is an inhibitor of the endothelin A receptor. In some embodiments the endothelin A receptor-targeting inhibitor is a competitor of the endothelin A or a fragment thereof. In some embodiments the endothelin A targeting inhibitor interacts in another way with the endothelin A receptor and/or the endothelin A or a fragment thereof, thereby inhibiting complement activation cascade.

In some embodiments the endothelin A receptor-targeting inhibitor of extravasation is selected from the group of peptides:

CAL1595, CAL1698, QGI10797, LNL2390, IVR2333, CAL2614, VLN2390, VLN2433, VLN2443 and TDP610 having the amino acid sequences as specified in SEQ IDs No. 28-37.

The one letter code amino acid sequences of said peptides are indicated in Table 4 of the examples further below.

e) Bone Morphogenetic Protein (BMP)

Complete blocking of the cytokine storm may not be advised, especially in case of viral and bacterial infection, as it could result in an iatrogenic immunodeficiency, and allow the infectious agents to propagate uncontrolled, causing a devastating outcome of the disease.

The inventor has opted for two elements to remedy this issue: the first is that they have designed and selected effector molecules that do not accumulate and break down rapidly, allowing a rapid tuning of the status of the cytokine storm; and the second element is that an additional target should be included that helps to heal the internal wound, a tissue damage accompanied by cell death, tissue disorganization to be restored in an enhanced and supported manner, as well as delay the invasion on fibroblast, preventing the irreversible tissue scarring that lead to loss of function in the affected organ.

Viral cytotoxicity, the system of tissue specific general complement activation, the passing of granulocytes through the endothelial layers from the capillaries into the shock organ parenchyma and cytokine-induced endothelial dysfunction individually and combined, cause massive loss of shock organ parenchyma cells, blood vessel integrity, and hemorrhage. In simple terms, this is a mechanism of making wounds inside the affected tissues in cytokine storm. With loss of tissue integrity, the organ becomes dysfunctional and in extreme cases that causes death. In less severe cases, the patients undergo a long process of wound healing. That process is slow, requires rebalancing of cytokines, and orchestrates the activity of stem cells, cell differentiation as well as invasion by various cell types, including fibroblasts. Unlike "standard" wounds, hemorrhaged tissues heal very slowly.

Fibroblasts appear very early in the hemorrhagic wounds, and cause fibrosis, scar formation that implies significant function loss in any affected organ. Fibrosis denotes excessive scarring, which exceeds the normal wound healing response to injury in tissues injured during cytokine storm.

It has been shown that bone morphogenetic proteins may regulate excess fibrosis. Therefore, in some embodiments of the present invention the therapeutic composition comprises a bone morphogenetic protein. In specific embodiments said bone morphogenetic protein is selected from bone morphogenetic protein BMP-6

Further, there are disclosed new recombinant bone morphogenetic proteins BMP and new active domains of bone morphogenetic proteins, and the specifications of said new recombinant bone morphogenetic proteins and the specifications of said new active domains of bone morphogenetic proteins are indicated in Tables 5 and 6 of the examples further below.

Therefore, in some embodiments of the present invention the therapeutic composition comprises a new recombinant bone morphogenetic protein BMP having an amino acid sequence as specified in one of the SEQ ID Nos. 38 to 40.

In further specific embodiments said recombinant bone morphogenetic protein is selected from a protein comprising an active domain having an amino acid sequence as specified in one of the SEQ ID Nos. 41 or 42 or from a protein comprising both of the two active domains having the amino acid sequences as specified in SEQ ID Nos. 41 and 42. Said protein may comprise in addition the specific leader sequences, hinge regions and anchor fragments as specified in table 6 below.

The present application also encompasses a nucleic acid encoding the recombinant bone morphogenetic proteins BMP. Further, it is disclosed a lentiviral vector comprising this nucleic acid. In addition, it is disclosed a plasmid comprising this nucleic acid and a cell line comprising said plasmid. Furthermore, it is disclosed a method of producing recombinant bone morphogenetic protein BMP by cultivating a cell comprising the plasmid.

In addition to the claimed composition, the present invention also encompasses a rationally designed method of treating a cytokine storm associated disorder. Particularly, it is disclosed a method of treating a cytokine storm associated disorder, characterized in that the method comprises administering an effective amount of at least one active agent selected from active agent groups a) to e):
    a) complement factor 3-targeting inhibitors,
    b) carboxypeptidase B enzymes,
    c) complement factor 5a receptor-targeting inhibitors,
    d) endothelin A receptor-targeting inhibitors,
    e) bone morphogenetic proteins.

The inventive method of treatment is a selection of a limited number or target molecules within the highly complex cascades of interrelated enzymes, mediators, and receptor and other proteins that when operating in concert, lead to the phenomenon known as cytokine storm.

Unlike general immune suppressions, depletion of complements system, plasmapheresis, irradiation and other interventions already in practice, this treatment leaves intact the functioning of the immune system, innate and antigen specific, essential to protection from the underlying viral or bacterial or fungal infections while enabling the fine tuning of the level of the functions necessary for the protective immunity by designing tools that are very short lived in the system and makes dangerous overdosing essentially impossible, as the active compounds (peptides and auto inactivating or naturally degrading proteins) never accumulate, rapidly clear from the circulations in hours, restoring the full functioning of the immune system and all of its components instantaneously.

The treatment consists of any one of the active components, any combination of two of the active components, any combination of 3 of active components, any combination of 4 active components, all 5 components of the active components that are intended to remedy the abnormality of the targets involved in the cytokine storm.

Particularly, it is disclosed a treatment or therapeutic composition for use in the treatment of COVID-19 and other cytokine storm associated disorders including either:
    a) complement factor 3-targeting inhibitor of complement activation cascade
    b) carboxypeptidase B enzyme
    c) complement factor 5a receptor-targeting inhibitor of complement activation cascade
    d) endothelin A receptor-targeting inhibitor of extravasation
    e) bone morphogenetic protein
alone, or combinations of 2, 3, 4 or 5 of said active agent a) to e), such as
    a) with either b), c), d) or e),
    b) with either c), d) or e),
    c) with either d) or e), or
    d) with e),
or combinations of
    a) with either b) and c), or with b) and d), or with b) and e),
    a) with either c) and d), or with c) and e),
    a) with d) and e),
    b) with either c) and d), or with c) and e), or with d) and e),
    c) with either d) and e),
or combinations of
    a) with either b), c) and d), or with c), d) and e),
    b) with either a), c) and e), or with a), d) and e),
    c) with either a), b) and d), or with b), d) and e),
or the combination of
    a) with b), c), d) and e).

The therapeutic composition of the present invention provides means for effectively treating COVID-19 and other cytokine storm associated disorders. In some embodiments of the invention the therapeutic composition used comprises at least two, three, four or five distinct active agents being selected from at least two, three, four or five of the active agent groups a) to e).

The treatment includes in some embodiments a formulation for delivery as a pH stabilized infusion that counteracts potential tissue acidification. In some embodiments the inventive composition is formulated with antiviral, antimicrobial agents. The inventive composition may be delivered as preventative intervention or as treatment for destructive cytokine storm.

The delivery of the active compounds of the treatment for controlling the cytokine storm may coincide with the need to use optional factors, depending on the root cause of the cytokine storm. Since the treatment coincides with the treatment of the root cause, we include additional supporting material to be added in the final embodiment of the invention.

In case of virus infection, antiviral treatment may be included. (In preferred implementation it is hydroxy chloroquine supplemented with Azithromycin and Zinc/Selenium)

In case of septic cases, properly selected antibiotics may be added.

In case of hemorrhagic shock, volume extenders, erythrocytes or other blood substitute may be added.

In case of microthrombus formation, anti-coagulants may be included

In case of adverse tissue acidification due to insufficient oxygen supply is a severe complicating factor and, therefore, high buffer capacity of bicarbonate may be added to the treatment to reduce the destructive effects of the acidification such as uncontrolled disseminated complement activation.

EXAMPLES

After selecting the targets, the inventor has designed and developed a series of highly specific compounds that meet the needs envisioned for the treatment of the overactive cytokine storm and break its positive feedback loops as well as moderate the tissue damage that it causes in the affected patients.

As an additional requirement, the inventor selected a series of solution relaying on short lived compound that do not accumulate, break down naturally without leaving potentially toxic molecules behind.

a) Complement Factor 3-Targeting Inhibitor of Complement Activation Cascade for Target 1

The inventor has designed a series of 19 peptides using a proprietary algorithm and the material composition is presented in table 1 below.

The peptides were synthesized by Fmoc solid phase method, purified on C18 reversa phase chromatography, tested by adding each peptide to and screened for complement inhibitory activity, in a simple antibody dependent hemolysis system in which 1 ug/mL of peptides were added to guinea pig complement, and were titrated against turkey erythrocytes mixed with hemolysin, a complement fixing anti-erythrocyte antibody solution. In the presence the peptides, the hemolythic activity of the complement was reduced, and the corresponding dilutions was determined. The inhibition was estimated by a formula:

Inhibition (%)=100−(dilution of sample titer*100)/dilution of control

TABLE 1

List of peptides and their complement inhibiting activity in a standard complement mediated hemolysis assay.

| Name | One letter code sequence | SEQ ID No. | Hemolysis inhibition (% of maximum) |
|---|---|---|---|
| AP1314 | APNHLLEVRV | 1 | >80 |
| LTA1309 | LTAYVVKVFSLA | 2 | >80 |
| DDL1619 | DDLKQLANGVDRYI | 3 | >80 |
| SDK1606 | SDKKGICVADPFEVT | 4 | >80 |
| SDA984 | SDAGLTFTSS | 5 | >80 |
| SDK1709 | SDKKGICVADPCFEVT | 6 | >80 |
| VQA1857 | VQAERSGIPIVTSPYQI | 7 | >80 |
| QAL1363 | QALPYSTVGNSNL | 8 | >40-60 |
| NIF1464 | NIFLKDSITTWE | 9 | >40-60 |
| LHL1431 | LHLSVRTLELRP | 10 | >40-60 |
| QRS1008 | QRSYTVAIA | 11 | >40-60 |
| KRP1057 | KRPQDAKNT | 12 | >20-40 |
| ERL1041 | ERLGREGVQ | 13 | >20-40 |
| LNC1538 | LNCQRYYGGGGYST | 14 | >20-40 |
| LSR1099 | LSRKVLLDGV | 15 | >20-40 |
| ESA1331 | ESASLRSEETKV | 16 | >20-40 |
| GQW1513 | GQWKIRAYYENS | 17 | ≤20 |
| IAV1501 | IAVHYLDETEQW | 18 | ≤20 |
| LRL1384 | LRLPYVVREQL | 19 | ≤20 |
| TAY1409 | TAYVVKVFSLAVN | 20 | ≤20 | b) Carboxypeptidase B Enzyme for the Target 2

By rapid activation of carboxypeptidase B with trypsin, the inventor has found that the carboxypeptidase B enzyme activity is very low in plasma. What is more, it is rapidly depleted as infection, hemorrhage, hypoxia develops, blood coagulation triggered (cf. FIG. 1), in each case when systemic complement activation occurs, resulting in allowing anaphylatoxins to act at their full potential to trigger the positive feedback that results in Cytokine storm.

Further experiments indicated that, in rats, the carboxypeptidase B activity is completely depleted during the early phase of hemorrhagic shock model in rats (in 100 minutes it is reduced nondetectable levels). Providing external carboxypeptidase B and restoring the depletion could significantly slow down the events leading to the onset of lethal cytokine storm.

To replenish the carboxypeptidase pool, the inventor designed a recombinant human zinc-metalloproteinase, using the gene for pre-procarboxypeptidase B, encoded by cpb1 gene. The deduced protein the inventor edited the deduced protein sequence, replaced the promoter with a proprietary one that is optimizes for fast and effective secretion of the preproprotein, and introduced a mutation that replaced the original T with a N amino acid at the activation cleavage site and reduced the intracellular toxicity of the preproprotein that enables the overexpression with rapid secretion and results in high yield production. The inventor left the internal inactivation site intact, therefore retained the expected natural inactivation times.

In another embodiment of the invention, human carboxypeptidase B2 (TAFI) is used for its highly similar enzyme activity. This enzyme has been reengineered in order to add a novel, improved secretory peptide, reduced the strength of its activation signal that is needed to convert the pre pro enzyme into an active enzyme as well as reduced the availability of the cryptic tryptic cleavage site in order to prolong its half life in the serum.

In the case of carboxypeptidase B1, the sequence was reverse translated into DNA and optimized for high yield overexpression in DG44 cells. A standard EF1 promoter was added for high efficiently and constitutive expression and built into a payload plasmid that is used for making a lentiviral expression vector to transduce a cell line.

Figure 3:
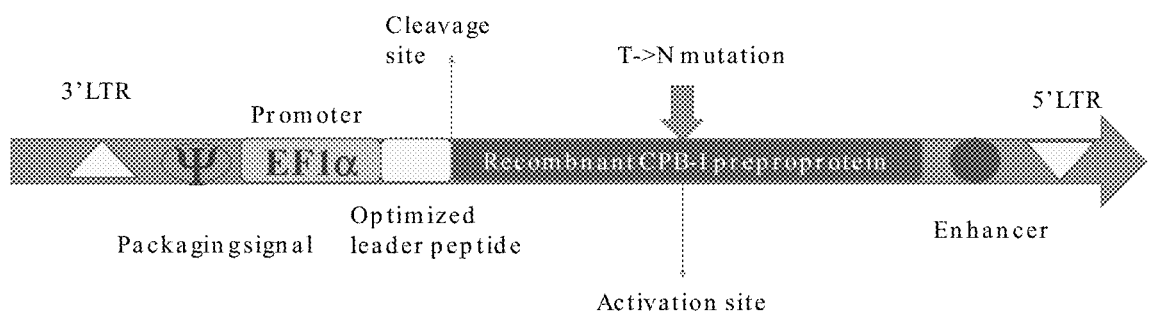
FIG. 3 shows the expression cassette designed for the recombinant human carboxypeptidase preproprotein expression.

The expression cassette designed for the recombinant human carboxypeptidase preproprotein expression is shown in FIG. 3. The expression cassette uses a plasmid backbone and resides the 3'-5' LTR regions. It contains a packaging signal (PSY) followed by a strong constitutive promoter (EF1 alpha). A new and improved leader peptide with improved cleavage site that enhances its secretion, followed by the optimized recombinant Carboxypeptidase B1 DNA sequence with triple stop codons, and a unique enhancer sequence.

The detailed specification of the obtained recombinant human carboxypeptidase B1 and B2 carboxypeptidase enzymes are shown in tables 2a and 2b below.

TABLE 2a

Specification of recombinant human carboxypeptidase B1 enzyme

| Item | Value | Comment |
|---|---|---|
| Name | CPB1 human carboxypeptidase B | Protein symbol |
| Gene ID in NBCI database | 1360 | |
| Locus | 3q24 | |
| Protein in UniProt Databse | P15086 (CBPB1_HUMAN) | |
| EC Number | 3.4.17.2 | |
| Complete wild type protein SEQ ID No. 49 | MLALLVLVTVALASAHHGGE \ HFEGEKVFRVNVEDENHINI IRELASTTQIDFWKPDSVTQ IKPHSTVDFRVKAEDTVTVE NVLKQNELQYKVLISNLRNV VEAQFDSRVRATGHSYEKYN KWETIEAWTQQVATENPALI SRSVIGTTFEGRAIYLLKVG KAGQNKPAIFMDCGFHAREW ISPAFCQWFVREAVRTYGRE IQVTELLDKLDFYVLPVLNI DGYIYTWTKSRFWRKTRSTH TGSSCIGTDPNRNFDAGWCE IGASRNPCDETYCGPAAESE KETKALADFIRNKLSSIKAY | |

TABLE 2a-continued

Specification of recombinant human carboxypeptidase B1 enzyme

| Item | Value | Comment |
|---|---|---|
| | LTIHSYSQMMIYPYSYAYKL GENNAELNALAKATVKELAS LHGTKYTYGPGATTIYPAAG GSDDWAYDQGIRYSFTFELR DTGRYGFLLPESQIRATCEE TFLAIKYVASYVLEHLY | |
| Leader SEQ ID No. 50 | MLALLVLVTVALASA | Wild type leader peptide |
| Recombinant Sequence SEQ ID No. 21 | MRAPAQIFGFLLLLFPGTCF AHHGGEHFEGEKVFRVNVED ENHINIIRELASTTQIDFWK PDSVTQIKPHSTVDFRVKAE DTVTVENVLKQNELQYKVLI SNLRNVVEAQFDSRVRANGH SYEKYNKWETIEAWTQQVAT ENPALISRSVIGTTFEGRAI YLLKVGKAGQNKPAIFMDCG FHAREWISPAFCQWFVREAV RTYGREIQVTELLDKLDFYV LPVLNIDGYIYTWTKSRFWR KTRSTHTGSSCIGTDPNRNF DAGWCEIGASRNPCDETYCG PAAESEKETKALADFIRNKL SSIKAYLTIHSYSQMMIYPY SYAYKLGENNAELNALAKAT VKELASLHGTKYTYGPGATT IYPAAGGSDDWAYDQGIRYS FTFELRDTGRYGFLLPESQI RATCEETFLAIKYVASYVLE HLY | New Leader peptide Activation pep. T→Q mutation Active domain |

TABLE 2b

Specification of recombinant human carboxypeptidase B1 enzyme

| Item | Value | Comment |
|---|---|---|
| Name | CPB2 human carboxypeptidase B2, TAFI | Protein symbol |
| Gene ID in Uniprot NBCI database | Q96IY4 | |
| ECC | EC:3.4.17.20 | |
| Protein in UniProt Database | | |
| EC Number | 3.4.17.2 | |
| Complete wild type protein SEQ ID No. 51 | MKLCSLAVLVPIVLFC \ EQHVFAFQSGQVLAAL PRTSRQVQVLQNLTTT YEIVLWQPVTADLIVK KKQVHFFVNASDVDNV KAHLNVSGIPCSVLLA DVEDLIQQQISNDTVS PRASASYYEQYHSLNE IYSWIEFITERHPDML TKIHIGSSFEKYPLYV LKVSGKEQTAKNAIWI DCGIHAREWISPAFCL WFIGHITQFYGIIGQY TNLLRLVDFYVMPVVN VDGYDYSWKKNRMWRK NRSFYANNHCIGTDLN RNFASKHWCEEGASSS | |

TABLE 2b-continued

Specification of recombinant human carboxypeptidase B1 enzyme

| Item | Value | Comment |
|---|---|---|
| | SCSETYCGLYPESEPE<br>VKAVASFLRRNINQIK<br>AYISMHSYSQHIVFPY<br>SYTRSKSKDHEELSLV<br>ASEAVRAIEKTSKNTR<br>YTHGHGSETLYLAPGG<br>GDDWIYDLGIKYSFTI<br>ELRDTGTYGFLLPERY<br>IKPTCREAFAAVSKIA<br>WHVIRNV | |
| Leader | See Uniprot<br>Q96IY4 | Wild type<br>leader peptide |
| Recombinant<br>Carboxypeptidase<br>B2 Sequence<br>SEQ ID No. 22 | MRAPAQIFGFLLLLFP<br>GTCFAFQSGQVLAALP<br>RTSRQVQVLQNLTTTY<br>EIVLWQPVTADLIVKK<br>KQVHFFVNASDVDNVK<br>AHLNVSGIPCSVLLAD<br>VEDLIQQQISNDTVSG<br>RASASYYEQYHSLNEI<br>YSWIEFITERHPDMLT<br>KIHIGSSFEKYPLYVL<br>KVSGKEQTAKNAIWID<br>CGIHAREWISPAFCLW<br>FIGHITQFYGIIGQYT<br>NLLRLVDFYVMPVVNV<br>DGYDYSWKKNRMWRKN<br>RSFYANNHCIGTDLNR<br>NFASKHWCEEGASSSS<br>CSETYCGLYPESEPEV<br>KAVASFLRRNINQIKA<br>YISMHSYSQHIVFPYS<br>YTRAKSKDHEELSLVA<br>SEAVRAIEKTSKNTRY<br>THGHGSETLYLAPGGG<br>DDWIYDLGIKYSFTIE<br>LRDTGTYGFLLPERYI<br>KPTCREAFAAVSKIAW<br>HVIRNV | New leader<br>Activation pep.<br>P→G mutation<br>Cryptic tryptic<br>site<br>S→A<br>Active site | c) C5a Receptor Inhibitor Peptides for Target 3

The antisense homology box peptide corresponding to region 10-27 in the C5a receptor PR10 (DYGHYDD-KDTLDLNTPVD; SEQ ID No. 26) did not inhibit the receptor activity, although it was demonstrated that it bound to two of its corresponding antisense peptides derived from C5a anaphylatoxin: peptides corresponding to amino acids 37-43 and 61-74.

The antisense homology box peptide PR101 (HWPFG-GAACSILPSLI, SEQ ID No. 27, Mw: 1782 corresponding to region 10-27 in the C5a receptor) did not affect the C5a-induced $Ca^{++}$ influx; however, it was found that this peptide strongly interacted with the albumin present in the culture medium causing its precipitation and aggregation.

A peptide fragment of the C5a receptor corresponding to the loop between the fifth and sixth hypothetical transmembrane regions (amino acids 226-245) that is antisense to C5a and is an intramolecular AHB in C5a receptor proved to be a weak antagonist of C5a when preincubated with C5a at high concentrations (>0.5 µM). It was shown by its ability to inhibit $Ca^{++}$ influx induced by C5a anaphylatoxin in C5a receptor-expressing (cAMP stimulated) U937 cells.

The same peptide fragment was shown to have C5a agonist activity as well, when U937 cells bearing the C5a receptor were preincubated with this peptide at a much lower concentration (even as little as 40 pM), the AHB peptide behaved as an agonist: Ca++ influx was efficiently triggered, even in the presence of an otherwise ineffective amount of C5a.

The AHB peptides derived from C5a anaphylatoxin, PL3 (QKKIEEIAAKYKHS, SEQ ID No. 52, Mw: 1670, C5a amino acids 3-16), PL12 (KYKHSVVKKSDGA, SEQ ID No. 53, Mw: 1801, C5a amino acids 12-27), PL37 (RAARISLGPRSIKAFTE, SEQ ID No. 54, Mw: 1985, C5a amino acids 37-51) and PL61 (LRANISHKDMQLGR, SEQ ID No. 55, Mw: 1740, C5a amino acids 61-74), were not able to inhibit C5a receptor in C5a-induced Ca++ influx assay.

The present invention includes methods and compositions that are designed to disable the ability of the C5a receptor to transmit cellular signals that are produced by binding of C5a to the receptor. One embodiment of the present invention is an inhibitory oligomer of peptides. One embodiment of the present invention consists of four repeats, the second consist of 8 monomers, collectively forming dendomer structure.

One specific monomer is a peptide of 17 amino acid long sequence derived from the C5a receptor itself. Each of the four monomers individually has a complex helical structure that forms spontaneously after the peptide is synthesized. Thus, the linear sequence of amino acids of each of the monomers which is manufactured in a peptide synthesizer at low cost, forms by itself into a more complex 3-dimensional structure, and the four or eight monomers are assembled during manufacture as a tetramer or octamer, or synthesized using a core in the form of for tetrameric dendromer X—K—$K_2$-(peptide)$_4$ or for Octameric dendromer: or X—K—$K_2$—$K_4$-(peptide)$_8$ (SEQ ID No. 69).

It is to be understood that although an oligomer with four repeats of the peptide is the most desired form of the present invention, oligomers with 2 through 16 repeats of the peptide are also affective in inhibiting C5a receptors. Another embodiment of the oligomer is the octameric repeat of the peptide.

Because of the particularly folded conformation of each monomer, and because of the additive effects of the four monomers, the tetramer fits perfectly with high affinity within the inner folded structure of the C5a receptor and blocks the ability of the receptor to induce damaging biological effects. The damaging caused by C5a effects that can be prevented by this compound include: the activation of granulocytes and release of tissue-injuring enzymes, constriction of blood vessels and capillaries which severely restrict the perfusion of tissues by blood, inflammation that changes vascular permeability, causes edema, attracts cells which in turn provoke severe tissue damage, and other effects that promote acute extension of myocardial infarcts.

The present invention is a C5a inhibitor that is differentiated from other products that inhibit C5a activity (such as antibodies or other proteins or peptides), that this construct will not only bind to C5a, reducing and neutralizing the available amount of C5a, but in the same time it binds to the C5a receptor, inhibiting its activity as a true C5a receptor inhibitor as well. This double-sided activity results in extremely powerful and efficient C5a inhibitor in that it substantially inactivates the C5a receptor's ability to function as a receptor. Other strategies currently being developed attempt to compete with C5a for binding to the receptor. A beneficial consequence of the present invention is the requirement of a very low effective concentration of the inhibitor to prolong the term of prevention of the damage caused by C5a by prolonged disabling of the receptors ability to function, while the low concentration of the present invention minimizes the potential side effects.

A distinct advantage of the present invention is that, because it inactivates the receptor itself, its effectiveness is not influenced by the local concentration of C5a. The inhibitor peptide is effective even in the presence of massive amounts of C5a that are typically generated during complement activation in the course of a heart attack or other adverse event. Other strategies that simply compete with C5a for binding to the C5a receptor can be overcome simply by increasing the local concentration of C5a to overwhelm the inhibitor. This inhibitor does not affect C5a binding and does not compete with the receptor-ligand interaction, rather affects the conformation of the C5aR and blocks its ability to transfer stimulatory information into the cell.

TABLE 3

List of C5a receptor inhibitor peptides

| Peptide ID | One letter code sequence | SEQ ID No. | | |
|---|---|---|---|---|
| LRT2463 | LRTWSRRATRSTKTLKVV | 23 | Monomeric | PR226 |
| LRT10353 | (LRTWSRRATRSTKTLKV V)$_4$K$_2$KV | 24, 43, and 44 | Tetrameric dendromer | PR226TET |
| LRT20707 | (LRTWSRRATRSTKTLKV V)$_8$K$_4$K$_2$KV | 25, 43, 44, and 45 | Octameric dendromer | PR226MAP |
| DYG2094 | DYGHYDDKDTLDLNTPVD | 26 | Monomeric | PR10 |
| HWP1667 | HWPFGGAACSILPSLI | 27 | Monomeric | PR101 |

Figure 2:
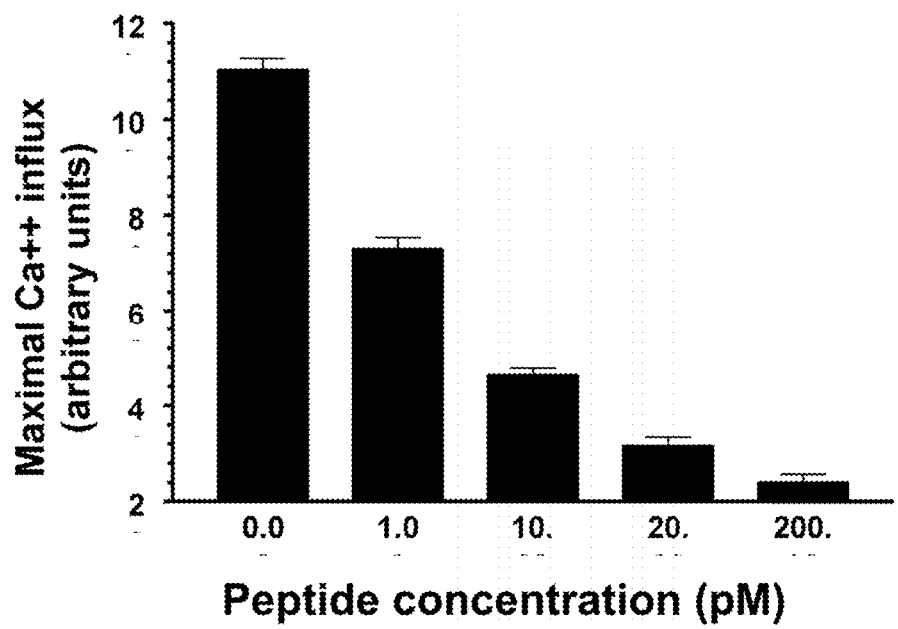
FIG. 2 shows the C5a receptor inhibitor activity of the peptide PR226MAP.

In FIG. 2 the activity is shown for PR226MAP, which is the most potent C5aR inhibitor. Particularly, it is shown the IC50 achieved at pM levels. Serial dilution of PR226 MAP peptide inhibited the C5a triggered Ca influx into the cells at femtomolar concentration levels, while the IC50 was as low as 1 pM. Complete inhibition was reached at 200 pM in this experiment. The reason is that the peptide immediately binds to the erythrocyte surfaces and forms a stable membrane bound pool, that is completely inert to erythrocytes, but upon contact with C5aR bearing cells, the inhibitory effect is fully exhibited. In addition, in the membrane bound state the peptide remains active for at least 12 hours. Therefore, it is a very effective C5aR inhibitor.

Further, it has been shown that the peptide can be delivered in vivo very safely, even at very high concentration. In FIG. 5 it is shown that an injection of 1 ug/kg PR226MAP peptide did not induce any cardiovascular change as represented by the same average blood pressure but abrogated the lethal effects of the subsequent challenge with the lethal dose of C5a.

Figure 6:
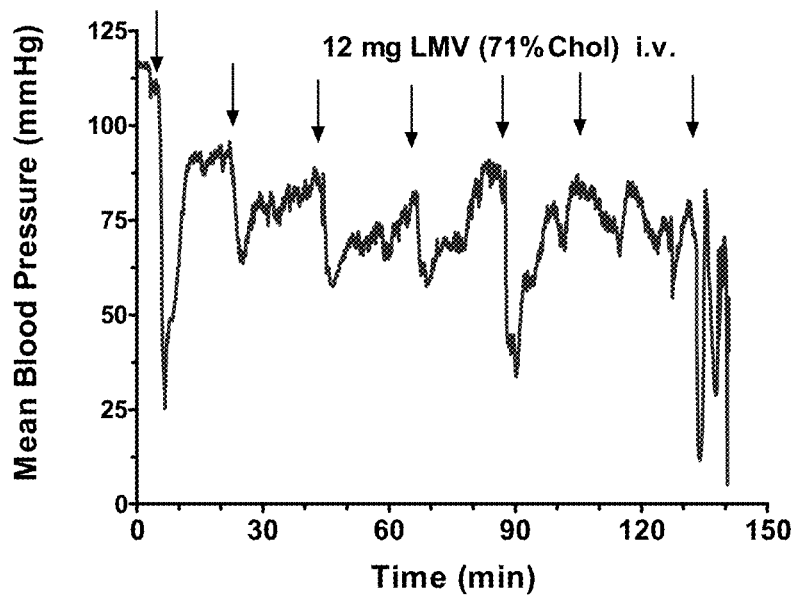
FIG. 6 shows that the animal survived 7 injections but developed acute hemorrhage and succumbed by the third hour displaying all the symptoms of acute cytokine storm.

FIG. 6 shows that the animal survived 7 injections but developed acute hemorrhage and succumbed by the third hour displaying all the symptoms of acute cytokine storm.

Figure 7A:
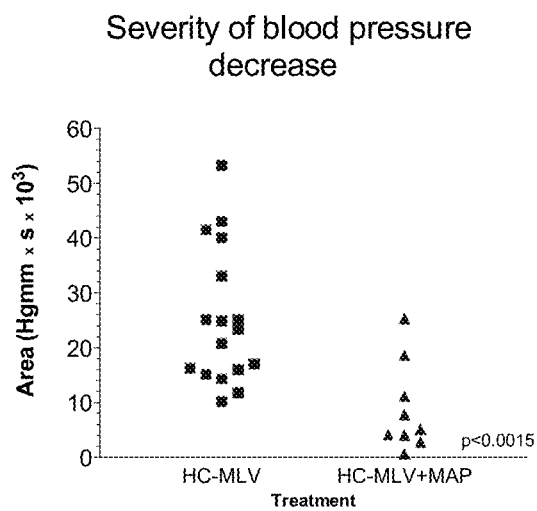
FIG. 7A shows the severity of blood pressure decrease in rats treated with the C5a receptor inhibitor peptide.
Figure 7B:
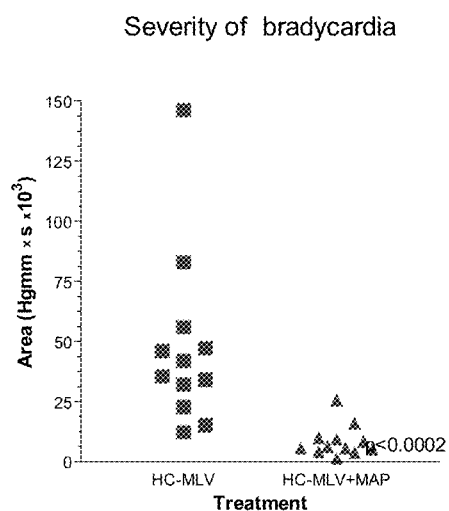
FIG. 7B shows the severity of bradycardia in rats treated with the C5a receptor inhibitor peptide.

FIGS. 7A and 7B show that the C5a receptor inhibitor peptide protects rats from the cardiovascular effects of the cytokine storm. The C5aR inhibitor blocked the hemodynamic and lethal effects of complement activation as well as the subsequent cytokine storm that manifested in cardiac collapse: bradycardia and severe fall of blood pressure, often cited as the fatal signs of the Cytokine storm.

d) The Endothelin Receptor Inhibitors for Target 4

The endothelin receptor is a complex of seven transmembrane helices and loops connecting them and belong to the family of the G-protein associated receptors the same family of receptors the C5a receptor is also a member. The inventor has run similar analysis and identified several antisense homology box peptides, using the same proprietary algorithm, and synthesis process (FMOC solid phase synthesis). The peptides and their variants have been produced and tested in standard functional endothelin assay in which external endothelin is added to prepared smooth muscles cells and the endothelin induced muscle contractility was measured. The peptides that inhibit the signal transduction by the receptor, are identified as Endothelin receptor inhibitors and are listed in Table 4 by their peptide ID, the amino acid sequence and their referenced name in the art.

TABLE 4

List of endothelin receptor A inhibiting peptides.

| Peptide ID | One letter code sequence | SEQ ID No. | Comment/name |
|---|---|---|---|
| CAL1595 | CALSVDRYRAVASW | 28 | ETR-P1 |
| CAL1698 | CALSVDRYRAVASWC | 29 | ETR-P1/cyc (cyclic) |
| QGI10797 | (QGIGIPLITAEI)$_8$K$_4$K$_2$KV | 30, 46, 47, and 48 | ERT-P3MAP |
| LNL2390 | LNLCALSVDRYRAVASWSRVI | 31 | ETR-P1/fl (extended) |
| IVR2333 | IVRSWSAVARYDSVLACLNLV | 32 | ETR-P1/fl.re (reversed sequence) |
| CAL2614 | CALSVDRYRAVASWGIPLITAIEI | 33 | ETR-P1/fl.sp |
| VLN2390 | VLNLCALSVDRYGAVASWSRVI | 34 | ETR-P1/fl.m1 |
| VLN2433 | VLNLCAGSVDRYRAVASWSRVI | 35 | ETR-P1/fl.m2 |
| VLN2443 | VLNLGALSVDRYRAVASWSRVI | 36 | ETR-P1/fl.m3 |
| TDP610 | (tryptamine-)DPVL | 37 | BQ123 |

One of the peptides was subsequently tested in dogs and confirmed its biological effect in vivo. Injecting dogs iv with 50 nm of ET-1 peptide resulted in a rapid increase in the concentration of the peptide: the normal baseline values of 2-3 fM increased to as high as 10-15 fM within 1 min and remained at high level for at least 10 min, followed by slow but steady decrease, but even after 30 min, the circulating endothelin level exceeded 6-7 fM. The elevated ET-1 level was marked with profound changes in circulation (details to be published elsewhere). However, pretreatment of dogs with 100 ug/kg ETR-P1/fl peptide removed the cardiovascular effects of injected ET-1 peptide from the circulation within 10 min and the measured endothelin level become normal. In spite of strong "buffering" effect of ETR-P141 peptide on externally administered ET-1 our data indicate that the peptide had a little or no influence (except a transient, 30-50% decrease) on the normal baseline level of ET peptide in the plasma. The explanation of this finding is that this peptide changed the conformation of the endothelin receptor, and that became capable of binding 4 times more ET-1 peptide, while frozen in an inactive conformation as far as receptor activation is concerned, indicating its high specificity, potency and stability that it can be applied in vivo. It is known in the previous art and has been patented and the patent expired.

The inventor also found that endothelin A receptor-targeting inhibitor of extravasation peptides do actively prevent leukocyte extravasation from circulation when stimulated by ET-1 in experimental system induced firm leukocyte adherence throughout the 90-minute observation period in animal models. The ETB-receptor antagonist IRL 1038 did not influence the number of sticking leukocytes in the submucosal postcapillary venules but transiently reduced the number of stickers in the collecting venules 30 minutes after ET-1 administration.

FIGS. 8A and 8B show the effective inhibition of smooth muscle contraction by the inventive peptides capable of blocking ET-A receptors.

e) The Recombinant Bone Morphogenetic Protein 6 for Target 5

By screening over 30,000 clones including the unmodified BMP6 expression system a 2-5 mg/L volumetric yield could be achieved. Therefore, the inventor designed a recombinant bone morphogenetic protein combining the fibroblast blocking and wound healing promoting effect of BMP 6 by molecular engineering. The protein was modified with novel leader peptide that was developed by the inventor. This new leader peptide improves secretion 4 times. Further, a modified activation site was engineered that reduces the activation and prevents the enzyme to be activated inside the cells and reduces its toxicity when overexpressed. With these modifications, extraordinary expression rates were achieved. Particularly, by screening of less than 180 clones, including the new recombinant bone morphogenetic protein, over 1 g/L volumetric productivity was achieved in a bioreactor. This allows the production of over 500-1000 purified human doses in a single mL of supernatant.

The expression cassette designed for the recombinant bone morphogenetic protein is shown in FIG. 4. The expression cassette uses a plasmid backbone and resides the 3'-5' LTR regions. It contains a packaging signal (PSY) followed by a strong constitutive promoter (EF1 alpha). A new and improved leader peptide with improved cleavage site that enhances its secretion, followed by the optimized recombinant bone morphogenetic protein 6 sequence with triple stop codons, and a unique enhancer sequence.

The material composition of the recombinant human Bone morphogenetic protein 6 (BMP6) has been improved by adding an optimized promoter and editing the sequence to reduce self-activation and the subsequent spontaneous inactivation of the protein by introducing a novel mutation at the activation site RRQQ→RRQA (SEQ ID Nos: 61 and 62, respectively).

TABLE 5

Specifications of recombinant human bone morphogenetic protein 6 (BMP6)

| Protein item | Value | Comment |
|---|---|---|
| Wild type BMP-6 protein sequence (BMP6_HUMAN) SEQ ID No. 56 | MAPFEPLASGILLLLWLICGPPPLRGene PPLPAAAAAAAGGQLLGDGGSPGRTBMP6 EQPPPSPQSSSGFLYRRLKTQEKRE MQKEILSVLGLPHRPRPLHGLQQPQ PPALRQQEEQQQQQQLPRGEPPPGR LKSAPLFMLDLYNALSADNDEDGAS EGERQQSWPHEAASSSQRRQPPPGA AHPLNRKSLLAPGSGSGGASPLTSA QDSAFLNDADMVMSFVNLVEYDKEF SPRQRHHKEFKFNLSQIPEGEVVTA AEFRIYKDCVMGSFKNQTFLISIYQ VLQEHQHRDSDLFLLDTRVVWASEE GWLEFDITATSNLWVVTPQHNMGLQ LSVVTRDGVHVHPRAAGLVGRDGPY DKQPFMVAFFKVSEVHVRTTRSASS RRRQQSRNRSTQSQDVARVSSASDY NSSELKTACRKHELYVSFQDLGWQD WIIAPKGYAANYCDGECSFPLNAHM NATNHAIVQTLVHLMNPEYVPKPCC APTKLNAISVLYFDDNSNVILKKYR NMVVRACGCH | |
| Old leader peptide SEQ ID No. 57 | MAPFEPLASGILLLLWLI | |
| New leader peptide SEQ ID No. 58 | MPGLGRRAQWLCWWWGLLCSC | Optimized |
| Propeptide SEQ ID No. 59 | CGPPPLRPPLPAAAAAAAGGQLLGD GGSPGRTEQPPPSPQSSSGFLYRRL KTQEKREMQKEILSVLGLPHRPRPL HGLQQPQPPALRQQEEQQQQQQLPR GEPPPGRLKSAPLFMLDLYNALSAD NDEDGASEGERQQSWPHEAASSSQR RQPPPGAAHPLNRKSLLAPGSGSGG ASPLTSAQDSAFLNDADMVMSFVNL VEYDKEFSPRQRHHKEFKFNLSQIP EGEVVTAAEFRIYKDCVMGSFKNQT FLISIYQVLQEHQHRDSDLFLLDTR VVWASEEGWLEFDITATSNLWVVTP QHNMGLQLSVVTRDGVHVHPRAAGL VGRDGPYDKQPFMVAFFKVSEVHVR TTRSASSRRR | |
| Active domain SEQ ID No. 60 | QQSRNRSTQSQDVARVSSASDYNSS ELKTACRKHELYVSFQDLGWQDWII APKGYAANYCDGECSFPLNAHMNAT NHAIVQTLVHLMNPEYVPKPCCAPT KLNAISVLYFDDNSNVILKKYRNMV VRACGCH | |
| Cleavage site Mutation SEQ ID Nos. 61 and 62 | RRQQ→RRQA | Weakened cleavage site |
| Complete Recombinant Human BMP-6 SEQ ID No. 38 | MPGLGRRAQWLCWWWGLLCSCCGPP PLRPPLAAAAAAAGGQLLGDGGSP GRTEQPPPSPQSSSGFLYRRLKTQE KREMQKEILSVLGLPHRPRPLHGLQ QPQPPALRQQEEQQQQQQLPRGEPP PGRLKSAPLFMLDLYNALSADNDED GASEGERQQSWPHEAASSSQRRQPP PGAAHPLNRKSLLAPGSGSGGASPL TSAQDSAFLNDADMVMSFVNLVEYD KEFSPRQRHHKEFKFNLSQIPEGEV VTAAEFRIYKDCVMGSFKNQTFLIS IYQVLQEHQHRDSDLFLLDTRVVWA SEEGWLEFDITATSNLWVVTPQHNM GLQLSVVTRDGVHVHPRAAGLVGRD GPYDKQPFMVAFFKVSEVHVRTTRS ASSRRQASRNRSTQSQDVARVSSA SDYNSSELKTACRKHELYVSFQDLG WQDWIIAPKGYAANYCDGECSFPLN AHMNATNHAIVQTLVHLMNPEYVPK PCCAPTKLNAISVLYFDDNSNVILK KYRNMVVR | |

Further, secretory and membrane attached forms of the recombinant human Bone Morphogenetic protein have been constructed.

TABLE 6

Specifications of recombinant human Bone morphogenetic protein 6 (BMP6)

| Item | Value |
|---|---|
| Wilde type human BMP 6 >sp\|P22004\|BMP6_HUMAN Bone morphogenetic protein 6 OS = Homo sapiens OX = 9606 GN = BMP6 PE = 1 SV = 1 SEQ ID No. 63 | MPGLGRRAQWLCWWWGLLCSCC GPPPLRPPLPAAAAAAAGGQLL GDGGSPGRTEQPPPSPQSSSGF LYRRLKTQEKREMQKEILSVLG LPHRPRPLHGLQQPQPPALRQQ EEQQQQQQLPRGEPPPGRLKSA PLFMLDLYNALSADNDEDGASE GERQQSWPHEAASSSQRRQPPP GAAHPLNRKSLLAPGSGSGGAS PLTSAQDSAFLNDADMVMSFVN LVEYDKEFSPRQRHHKEFKFNL SQIPEGEVVTAAEFRIYKDCVM GSFKNQTFLISIYQVLQEHQHR DSDLFLLDTRVVWASEEGWLEF DITATSNLWVVTPQHNMGLQLS VVTRDGVHVHPRAAGLVGRDGP YDKQPFMVAFFKVSEVHVRTTR SASSRRQQSRNRSTQSQDVAR VSSASDYNSSELKTACRKHELY VSFQDLGWQDWIIAPKGYAANY CDGECSFPLNAHMNATNHAIVQ TLVHLMNPEYVPKPCCAPTKLN AISVLYFDDNSNVILKKYRNMV VRACGCH |
| Wilde type human BMP7 >sp\|P18075\|BMP7_HUMAN Bone morphogenetic protein 7 OS = Homo sapiens OX = 9606 GN = BMP7 PE = 1 SV = 1 SEQ ID No. 64 | MHVRSLRAAAPHSFVALWAPLF LLRSALADFSLDNEVHSSFIHR RLRSQERREMQREILSILGLPH RPRPHLQGKHNSAPMFMLDLYN AMAVEEGGGPGGQGFSYPYKAV FSTQGPPLASLQDSHFLTDADM VMSFVNLVEHDKEFFHPRYHHR EFRFDLSKIPEGEAVTAAEFRI YKDYIRERFDNETFRISVYQVL QEHLGRESDLFLLDSRTLWASE EGWLVFDITATSNHWVVNPRHN LGLQLSVETLDGQSINPKLAGL IGRHGPQNKQPFMVAFFKATEV HFRSIRSTGSKQRSQNRSKTPK NQEALRMANVAENSSSDQRQAC KKHELYVSFRDLGWQDWIIAPE GYAAYYCEGECAFPLNSYMNAT NHAIVQTLVHFINPETVPKPCC APTQLNAISVLYFDDSSNVILK KYRNMVVRACGCH |
| Wilde type leader peptide SEQ ID No. 65 | MPGLGRRAQWLCWWWGLLCS (removed) |
| Optimized leader peptide SEQ ID No. 66 | MRAPAQIFGFLLLLFPGTCFA (added) |
| Recombinant BMP7 active domain I with inserts from BMP6 SEQ ID No. 41 | CCGPPPLRPPLPAAAAAAAGGQ LLGDGGSPGRTEQPPPSPQSSS GFLYRRLKTQEKREMQKEILSV LGLPHRPRPLHGLQQPQPPALR QQEEQQQQQQLPRGEPPPGRLK SAPLFMLDLYNALSADNDEDGA SEGERQQSWPHEAASSSQRRQP PPGAAHPLNRKSLLAPGSGSGG ASPLTSAQDSAFLNDADMVMSF VNLVEYDKEFSPRQRHHKEFKF NLSQIPEGEVVTAAEFRIYKDC VMGSFKNQTFLISIYQVLQEHQ HRDSDLFLLDTRVVWASEEGWL EFDITATSNLWVVTPQHNMGLQ LSVVTRDGVHVHPRAAGLVGRD GPYDKQPFMVAFFKVSEVHVRT TRSASSRRR |
| Active domain II SEQ ID No. 42 | QQSRNRSTQSQDVARVSSASDY NSSELKTACRKHELYVSFQDLG WQDWIIAPKGYAANYCDGECSF PLNAHMNATNHAIVQTLVHLMN PEYVPKPCCAPTKLNAISVLYF DDNSNVILKKYRNMVVRACGCH |
| Human IgG Hinge region SEQ ID No. 67 | RWPESPKAQASSVPTAQPQAEG SLAKATAPATTRNTGRGGEEKK KEKEKEEQEERETKTPECP |
| Human CD59 PI anchor SEQ ID No. 68 | QCYNCPNPTADCKT AVNCSSDFDA CLITKAELGY HYVAQAGRRQ SSHFSLLKCW DYRCEPSHWP HCPYFNWGYKCITSVGSLSI AISTTSQPA |
| Complete recombinant BMP sequence for secretory production SEQ ID No. 39 | MRAPAQIFGFLLLLFPGTCFAC CGPPPLRPPLPAAAAAAAGGQL LGDGGSPGRTEQPPPSPQSSSG FLYRRLKTQEKREMQKEILSVL GLPHRPRPLHGLQQPQPPALRQ QEEQQQQQQLPRGEPPPGRLKS APLFMLDLYNALSADNDEDGAS EGERQQSWPHEAASSSQRRQPP PGAAHPLNRKSLLAPGSGSGGA SPLTSAQDSAFLNDADMVMSFV NLVEYDKEFSPRQRHHKEFKFN LSQIPEGEVVTAAEFRIYKDCV MGSFKNQTFLISIYQVLQEHQH RDSDLFLLDTRVVWASEEGWLE FDITATSNLWVVTPQHNMGLQL SVVTRDGVHVHPRAAGLVGRDG PYDKQPFMVAFFKVSEVHVRTT RSASSRRQQSRNRSTQSQDVA RVSSASDYNSSELKTACRKHEL YVSFQDLGWQDWIIAPKGYAAN YCDGECSFPLNAHMNATNHAIV QTLVHLMNPEYVPKPCCAPTKL NAISVLYFDDNSNVILKKYRNM VVRACGCH |
| Complete recombinant BMP sequence for cell surface and exsosome expression SEQ ID No. 40 | MRAPAQIFGFLLLLFPGTCFAQ QSRNRSTQSQDVARVSSASDYN SSELKTACRKHELYVSFQDLGW QDWIIAPKGYAANYCDGECSFP LNAHMNATNHAIVQTLVHLMNP EYVPKPCCAPTKLNAISVLYFD DNSNVILKKYRNMVVRACGCHR WPESPKAQASSVPTAQPQAEGS LAKATAPATTRNTGRGGEEKKK EKEKEEQEERETKTPECPQCYN CPNPTADCKTAVNCSSDFDACL ITKAELGYHYVAQAGRRQSSHF SLLKCWDYRCEPSHWPHCPYFN WGYKCITSVGSLSIAISTTSQP A |

Abbreviations and Definitions

| Term | Definition/comment |
|---|---|
| nCOV- | New coronavirus or SARS nCOV-2 coronavirus causing COVID-19 disease |
| CoVid-19 | The disease caused by the SARS nCOV-2 virus |
| ARDS | Acute respiratory disease |
| MERS | Middle Eastern Respiratory Syndrome Virus |
| SARS | Severe Acute Respiratory syndrome Virus |
| Spike protein | Surface glycoprotein of Severe acute respiratory syndrome [nCOV-2 |

| Term | Definition/comment |
|---|---|
| C5aR | C5a Receptor |
| CD88 | C5a Receptor |
| C5a | Complement factor 5 derived anaphylatoxin |
| C4a | Complement factor 4 derived anaphylatoxin |
| C3a | Complement factor 3 derived anaphylatoxin |
| IV IgG | Intravenous Immunoglobulin G |
| PIF | Phagocytosis Inhibitor Factor |

The inventive peptides disclosed herein are defined by their amino acid sequence as presented respectively. The present invention also includes the following modifications thereof.

Qa—place amino acids here-Qc", wherein Q" is selected from the group consisting of hydrogen, alkyl, aryl, arylalkyl, alkyloyl, aryloyl, arylalkyloyl, alkyloxoyl, aryloxoyl and arylalkyloxoyl; and QC is selected from the group consisting of hydroxy, alky loxy, aryloxy, arylalkyloxy, alkylamino, dialkylamino, ary lamino, diarylamino, (aryl)(alkyl)amino, arylalkylamino, diarylalkylamino, (alkyl)(arylalkyl)amino, (aryl)(arylalky l)amino, and amino. Preferably Qa" is hydrogen and QC is hydroxy, i.e., H—place amino acids here —OH. Preferably Q" is H3C—C(O)— and QC is amino, i.e., H3C—C(O)—place amino acids here —NHZ. In another embodiment of the invention, the anti-wrinkle agent is a peptide having the amino acid sequence Qa-amino acids-Q", wherein Q" is selected from the group. In addition a peptide can be synthesis in dendromer form, where the peptide is described by the (Qa-place amino acids here-Q)$_8$ K$_4$K$_2$K-x formula of dendromeric branching structure. With Qa consisting of hydrogen, alkyl, aryl, arylalkyl, alkyloyl, ary~loyl, arylalkyloyl, alkyloxoyl, aryloxoyl and arylalkyloxoyl; and QC is selected from the group consisting of hydroxy, alkyloxy, aryloxy, arylalkyloxy, alkylamino, dialkylamino, arylamino, diarylarnino, (aryl)(alkyl)amino, arylalkylamino, diarylalkylamino, (alkyl)(arylalkyl)amino, (aryl)(arylalky l)amino, and amino. Preferably Qa, is hydrogen and QC is hydroxy To obtain the proper list of derivatives, replace the place holder amino acid sequence with each the listed amino acid sequence of the inhibitor peptides claimed in this invention.

As used herein, "alkyl" and "R" mean a hydrocarbon chain which may be straight, or branched; substituted (mono- or pot y-) or unsubstituted, preferably unsubstituted; saturated or monounsaturated (i.e., one double or triple bond in the chain), or polyunsaturated (i.e., two or more double bonds in the chain, two or more triple bonds in the chain, or one or more double and one or more triple bonds in the chain). As used herein, "aryl" and "Ar" mean an aromatic; substituted (mono- or poly-) or unsubstituted, preferably unsubstituted. Preferred aryls are phenyl, pyridyl, pynnidyl and napthyl; more preferred is phenyl. As used herein, "arylalkyl" means Ar—R—. As used herein, "alkyloyl" means R—C(O)— As used herein, "aryloyY" means Ar—C(O). As used herein, "arylalkyloyl" means Ar—R—C(O)—. As used herein, "alkyloxoyl" means R—O—C(O)—. As used herein, "aryloxoyl" means Ar—O—C(O)—. As used herein, "arylalkyloxoyl" means Ar—R—O—C(O)—. As used herein, "alkyloxy" means R—O—. As used herein, "aryloxy" means Ar—O—. As used herein, "arylalkyloxy" means Ar—R—O—. As used herein, "alkylamino" means R—N(H). As used herein, "dialkylamino" means R2N—. As used herein, "arylamino" means Ar—N(H)—. As used herein, "diarylamino" means (Ar)2N—. As used herein, "(aryl)(alkyl)amino" means Ar—N(R)—. As used herein, "arylalkylamino" means Ar—R— N(H)—. As used herein, "diarylalkylamino" means (Ar—R)2N—. As used herein, "(alkyl)(arylalkyl) amino" means Ar—R—N(R)—. As used herein, "(aryl)(arylalkyl)amino" means Ar—R—N(R)—.

The invention claimed is:

1. A therapeutic composition comprising an active agent comprising SEQ ID NO: 1.

2. The therapeutic composition according to claim 1, further comprising at least one additional active agent.

3. The therapeutic composition according to claim 2, wherein the at least one additional active agent comprises at least one of SEQ ID NOs: 1-20.

4. The therapeutic composition according to claim 2, wherein the at least one additional active agent comprises at least one carboxypeptidase B (EC 3.4.16-3.4.18), or a recombinant carboxypeptidase B enzyme comprising SEQ ID NO: 21 or SEQ ID NO. 22.

5. The therapeutic composition according to claim 2, wherein the at least one additional active agent comprises at least one SEQ ID NOs.

6. The therapeutic composition according to claim 2, wherein the at least one additional active agent comprises at least one peptide selected from SEQ ID NOs: 28-37.

7. The therapeutic composition according to claim 2, wherein the at least one additional active agent comprises at least one bone morphogenetic protein BMP-6, or a recombinant BMP comprising one of SEQ ID NOs: 38-42 or one of SEQ ID Nos. 41 or 42.

* * * * *